Figure 1:
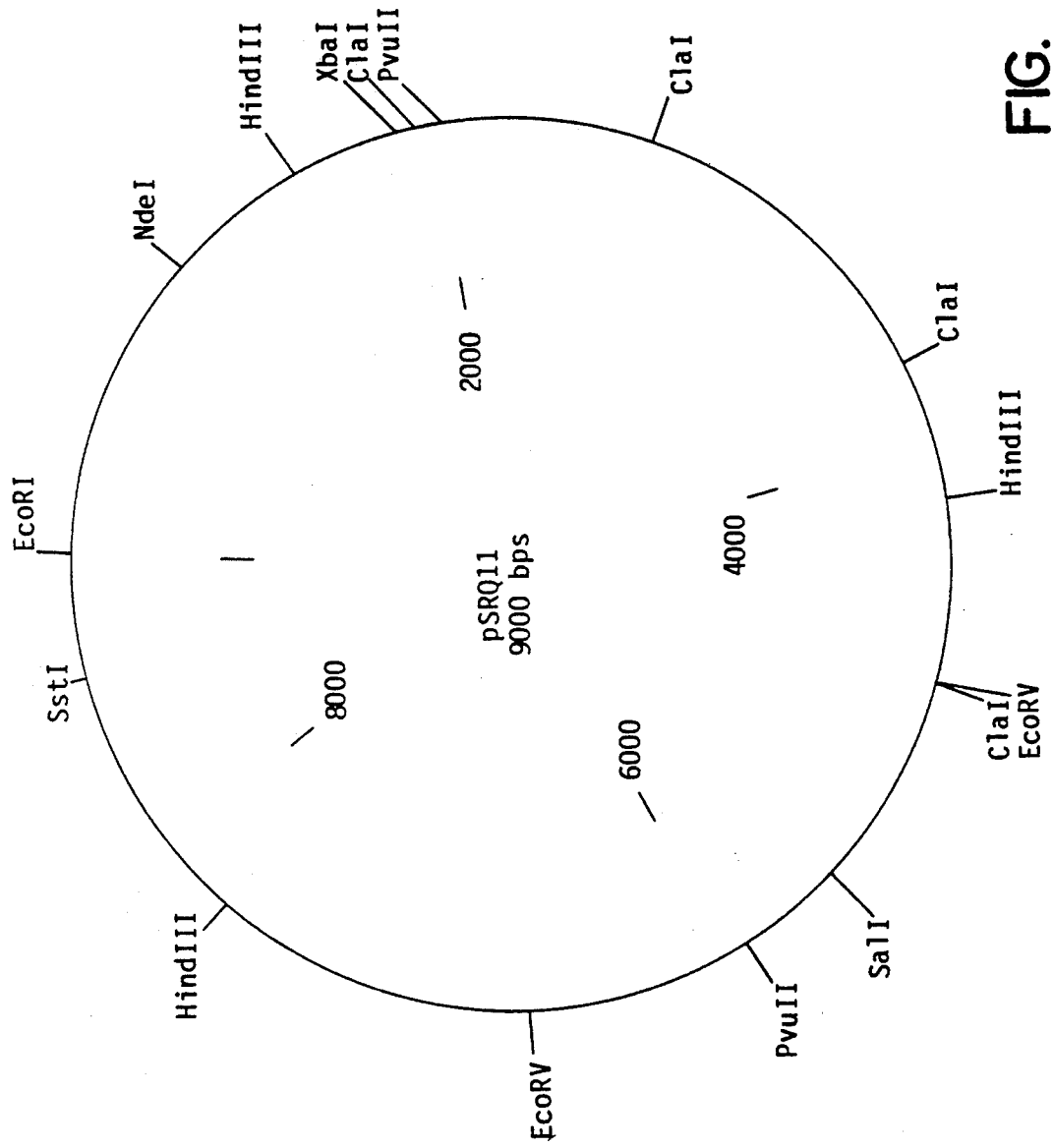

United States Patent [19]

Marugg et al.

[11] Patent Number: 5,260,212

[45] Date of Patent: Nov. 9, 1993

[54] **CLONED GENE ENCODING FOR BACTERIOCIN FROM *PEDIOCOCCUS ACIDILACTICI***

[75] Inventors: John D. Marugg, Utrecht, Netherlands; Adrianus M. Ledeboer; Peter A. Vandenbergh, both of Sarasota, Fla.; James T. Henderson, Bradenton, Fla.

[73] Assignee: Quest International Flavors & Food Ingredients Co., Division of Indopco, Bridgewater, N.J.

[21] Appl. No.: 635,965

[22] Filed: Dec. 31, 1990

Related U.S. Application Data

[63] Continuation-in-part of Ser. No. 375,344, Jul. 3, 1989, abandoned, which is a continuation-in-part of Ser. No. 12,619, Feb. 9, 1987, Pat. No. 4,883,673, and a continuation-in-part of Ser. No. 514,102, Apr. 25, 1990.

[51] Int. Cl.⁵ .................... C12N 15/31; C12N 15/63
[52] U.S. Cl. ................ 435/252.3; 435/320.1; 435/69.1; 536/23.7
[58] Field of Search ............... 435/252.3, 320.1; 536/27; 530/350

[56] References Cited

U.S. PATENT DOCUMENTS 4,883,673  11/1989  Gonzalez ................ 424/195.1
4,929,445   5/1990  Vandenbergh et al. ........ 424/195.1

OTHER PUBLICATIONS

Gonzalez, C. F., and B. S. Kunka, Appl. Environ. Microbiol. 53:2534-2538 (1987).
Mundt, J. O., W. G. Beattie, and F. R. Wieland, J. Bacteriol. 98:938-942 (1969).
Pederson, Bacteriol. Rev. 13:225-232 (1949).
Smith, J. L., and S. A. Palumbo, J. Food Prot. 46:997-1006 (1983).
Gonzalez, C. F., and B. S. Kunka, Appl. Environ. Microbiol. 46:81-89 (1983).
Graham, D. C., and L. L. McKay, Appl. Environ. Microbiol. 50:532-534 (1985).
Raccach, M., CRC Crit. Rev. Microbiol. 14:291-309 (1987).
Gonzalez, C. F., and B. S. Kunka, Appl. Environ. Microbiol. 51:105-109 (1986).
Daeschel, M. A., and T. R. Klaenhammer, Appl. Environ. Microbiol. 50:1538-1541 (1985).
Bhunia et al, J. Applied Bact. 65:261-268 (1988).
Pucci, M. P., E. R. Vedamuthu, B. S. Kunka and P. A. Vandenbergh, Appl. Environ. Microbiol. 54:2349-2353 (1988).
Berry, E. D., et al., J. Food Protection 53:194-197 (1990).
Nielsen, J., et al., Appl. Environ. Microbiol. 56, 2142-2145 (1990).
Gilmore, M. S., Curr. Top. Microbiol. Immunol. 118:219-234 (1985).
Robeson, J. P., et al., J. Bacteriol. 153:211-221 (1983).
Smorawinska, M., et al., J. Bacteriol. 153:1095-1097 (1983).
Chemical Engineering News pp. 36-46 Oct. 1, 1990.
Bolivar, F., et al., Gene 2:95-113 (1977).
Chang, A. C. Y., et al., J. Bacteriol. 134:1141-1156 (1978).
Dao, My Lien, et al., Applied and Environmental Microbiology, 49:115-119 (Jan. 1985).
Macrina, Francis L., et al., Gene, 19:345-353 (1982).
Macrina, Francis L., et al., Gene, 25:145-150 (1983).
Tobian, Janet Ash, et al., Journal of Bacteriology 160:556-563 (Nov. 1984).

(List continued on next page.)

*Primary Examiner*—Robert J. Hill, Jr.
*Assistant Examiner*—John D. Ulm
*Attorney, Agent, or Firm*—Ian C. McLeod

[57] ABSTRACT

Isolation and identification of a gene encoding for a bacteriocin precursor in *Pediococcus acidilactici*, cloning of the gene in a vector plasmid and transformation to bacteria is described. The bacteriocin is particularly useful for inhibiting Listeria in food products.

23 Claims, 23 Drawing Sheets

```
SalI
GTCGACCGGA AATGATCTTT TTAACATCCA AGATAAAGAA AGCAAAATAG CTAAACAGAA    60

GATTGTTAAA TCTGGTAGTA ATAAAGATGG CATACACACA AATAGAGCTA TTAAACGCTG   120

GTGGAAATTC TGGTAAAAGT TAATGTAAGC CTTAAGGTTT CAACTAAAGC AATTACAGTC   180

AACCATAACC ATAGTATTGG ATTGTCATTT TATTGGCTAT AAAATAGTAA ATCAGTGAAT   240

TTCATTACAA AAGGGCTCAC AAAAAATTGT TTTCTTCCTC CAACAATAGC GAGACGCTTT   300

TCTAATTGCT TGACCCAAAG AGCAATAGAA TATTTTGAAG GTCCAAATTA TTCTGTTAAT   360

GATTTAAGTG AACGGCCTTC TTGGTGAAAT TTAACCAATG AATCTTTGAA ATCTTGTGAA   420

TAACGAATTG ACATAAAAAT GCTCCTATAT TTTCATTTTA CGGACTGAAT AAAAATAGTC   480
```

OTHER PUBLICATIONS

Backman, K., et al., Proc. Natl. Acad. 73. 4174–4178 (1976).
Maniatis, T., et al., Molecular cloning: a laboratory manual. Cold Spring Harbor Lab., Cold Spring Harbor, N.Y. (1982).
Clewell, D. B., and D. R. Helinski, Biochemistry 9:4428–4440 (1970).
LeBlanc, D. J., and L. N. Lee, J. Bacteriol. 140:1112–1115 (1979).
Macrina, F. L., et al., Plasmid 1:417–420 (1978).
Sanger, F., et al., Proc. Natl. Acad. Sci. USA 74:5462–5467 (1977).
Biggin, M. D., et al., Proc. Natl. Acad. Sci. USA, 80:3963–3965 (1983).
Hattori and Sakaki, Anal. Biochem., 152:232–238 (1986).
Barone, A. D., et al., Nucleic Acid Research. 12:4051–4061 (1984).

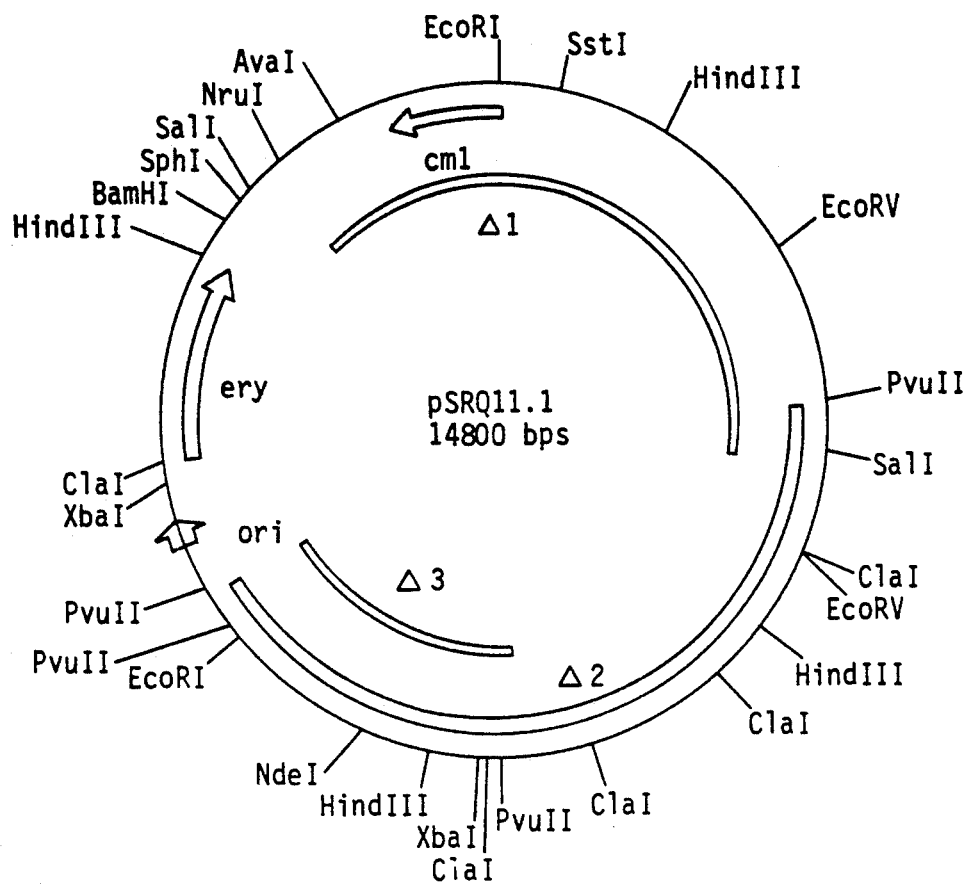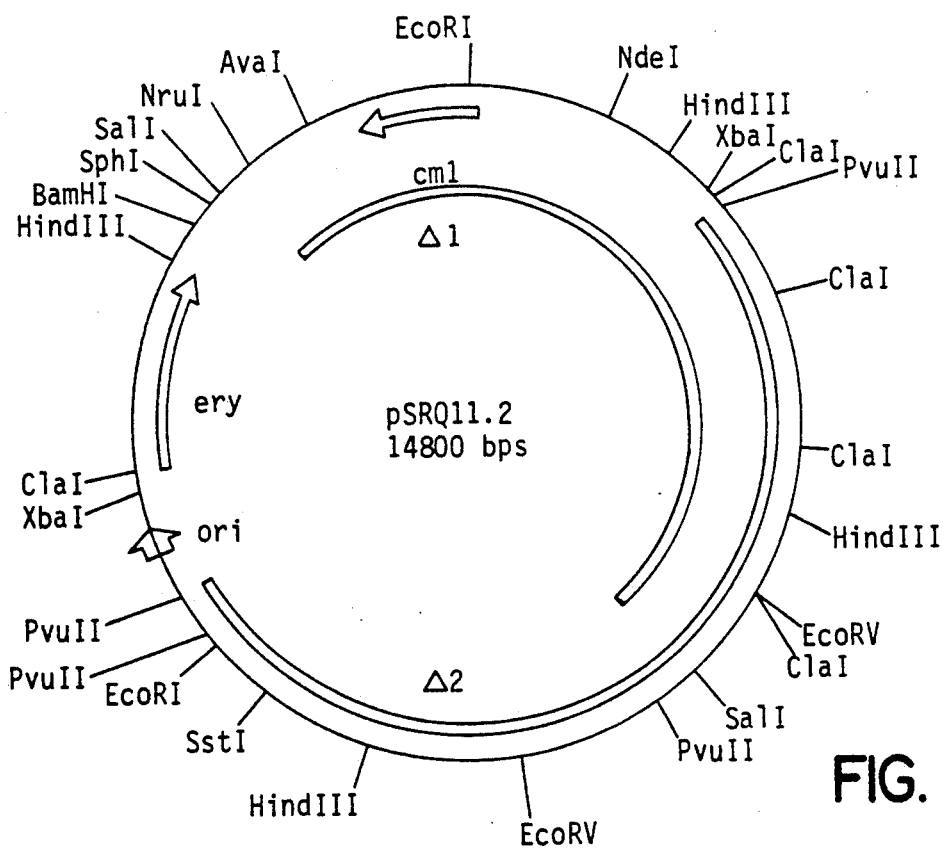
FIG. 2

FIG. 4A

```
SalI
GTCGACCGGA AATGATCTTT TTAACATCCA AGATAAAGAA AGCAAATAG CTAAACAGAA    60

GATTGTTAAA TCTGGTAGTA ATAAAGATGG CATACACACA AATAGAGCTA TTAAACGCTG   120

GTGGAAATTC TGGTAAAAGT TAATGTAAGC CTTAAGGTTT CAACTAAAGC AATTACAGTC   180

AACCATAACC ATAGTATTGG ATTGTCATTT TATTGGCTAT AAAATAGTAA ATCAGTGAAT   240

TTCATTACAA AAGGGCTCAC AAAAAATTGT TTTCTTCCTC CAACAATAGC GAGACGCTTT   300

TCTAATTGCT TGACCCAAAG AGCAATAGAA TATTTTGAAG GTCCAAATTA TTCTGTTAAT   360

GATTAAGTG AACGGCCTTC TTGGTGAAAT TTAACCAATG AATCTTTGAA ATCTTGTGAA   420

TAACGAATTG ACATAAAAAT GCTCCTATAT TTTCATTTTA CGGACTGAAT AAAAATAGTC   480
```

```
CATTTTTTTA GTATAAGAGC AGTAAAACCA GACGTGGAAA CCACGTGGTC TTTTAGTTGA  540

TTCAGTAAAA GAAGCCGAAA CCAACGTTTT CACGTTGGTT TCGGCTTCTT TGGCTTTTAA  600

TTGCGGGAAC GCACACAAAG AGGCAAAAAA GATTTGATAA AATCAAAGCT AGAAACTAGC  660

TCCGGTCATG CTTGTTGCGA TCATTATCGC GTAAGTCTTC TACGTGGGCA TCACCACTCG  720

TATCGATATC TAGTTCTTCG CGGCCGACGT TTTCACTTAC TTGTTTCATA TCTTCGTGTT  780

CTTGTTTACG AATGTTAACT TCTTCTCGAA CGACCGGGCG TTTGTTGACA TCGGTAGTTG  840

CAGCCGCACC ATCTCCGGGC TTTCTTTCGA TCACGATTTC TTCTCGTTTA AAATGAATAT  900
```

FIG. 4B

```
ATAAACTGTG TCATAACTTA AAAGATACTG CGTTGATAGC CAGGTTTCAA AAATTGACCA   960

AGATCGTTAA CCAGTTTTGG TGCGAAAATA TCTAACTAAT ACTTGACATT TAAATTGAGT  1020

ORF1
GGGAACTAGA ATAAGCGCGT ATTAAGAAG AAGGAGATTT TTGTG ATG                1078
                                                  Met

AAA AAA ATT GAA AAA TTA ACT GAA AAA GAA ATG GCC AAT ATC ATT GGT    1126
Lys Lys Ile Glu Lys Leu Thr Glu Lys Glu Met Ala Asn Ile Ile Gly
       -15                     -10                      -5

→ GGT AAA TAC TAC GGT AAT GGG GTT ACT TGT GGC AAA CAT TCC TGC TCT   1174
  Gly Lys Tyr Tyr Gly Asn Gly Val Thr Cys Gly Lys His Ser Cys Ser
   1                   5                      10                  15

GTT GAC TGG GGT AAG GCT ACC ACT TGC ATA ATC AAT AAT GGA GCT ATG    1222
Val Asp Trp Gly Lys Ala Thr Thr Cys Ile Ile Asn Asn Gly Ala Met
                 20                      25                  30

GCA TGG GCT ACT GGT GGA CAT CAA GGT AAT CAT AAA TGC                1261
Ala Trp Ala Thr Gly Gly His Gln Gly Asn His Lys Cys
         35                      40
```

FIG. 4C

```
                                          ORF2
*
TAGCATTATG CTGAGCTGGC ATCAATAAAG GGGTGATTTT ATG AAT AAG ACT AAG   1316
                                           Met Asn Lys Thr Lys
                                            1               5

TCG GAA CAT ATT AAA CAA CAA GCT TTG GAC TTA TTT ACT AGG CTA CAG   1364
Ser Glu His Ile Lys Gln Gln Ala Leu Asp Leu Phe Thr Arg Leu Gln
              10                  15                  20

TTT TTA CTA CAG AAG CAC GAT ACT ATC GAA CCT TAC CAG TAC GTT TTA   1412
Phe Leu Leu Gln Lys His Asp Thr Ile Glu Pro Tyr Gln Tyr Val Leu
              25                  30                  35

GAT ATT CTG GAG ACT GGT ATC AGT AAA ACT AAA CAT AAC CAG CAA ACG   1460
Asp Ile Leu Glu Thr Gly Ile Ser Lys Thr Lys His Asn Gln Gln Thr
              40                  45                  50
```

FIG. 4D

FIG. 4E

```
CCT GAA CGA CAA GCT CGT GTA GTC TAC AAC AAG ATT GCC AGC CAA GCG     1508
Pro Glu Arg Gln Ala Arg Val Val Tyr Asn Lys Ile Ala Ser Gln Ala
            55                  60                  65

TTA GTA GAT AAG TTA CAT TTT ACT GCC GAA GAA AAC AAA GTT CTA GCA     1556
Leu Val Asp Lys Leu His Phe Thr Ala Glu Glu Asn Lys Val Leu Ala
70                  75                  80                  85

GCC ATC AAT GAA TTG GCG CAT TCT CAA AAA GGG TGG GGC GAG TTT AAC     1604
Ala Ile Asn Glu Leu Ala His Ser Gln Lys Gly Trp Gly Glu Phe Asn
                90                  95                  100

ATG CTA GAT ACT ACC AAT ACG TGG CCT AGC CAA TAGTACTGAT AAAGGGGATA  1657
Met Leu Asp Thr Thr Asn Thr Trp Pro Ser Gln
        105                 110
```

```
TTGTAGTTGT CTAAGAAAT TTTGGTCAAAT ATCTTTTTAG CATTAGGCGT CTTTCTTGCT 1717

TTTGCAGGAG TTGCTACCA TATCGGTGAGT GCTGACAGTT CCGCTACTAT AGAATCAAAT 1777

ACTAGCTCGA AAATCATCG ATGGTGCAACT TATGAAGAAA ACATCAGGGG CGTTATTCCT 1837

ATTACGCTAA CTCAATATT TGCATAAAGCT CAAACTGGAG AAAAATTTAT TGTCTTTGTC 1897

GGGTTCAAGG AGTGTGTGC ATTGTCGTAAA TTTTCTCCAG TCATGAAACA ACGGGTCTTT CAGCATGGCT 2017

CAAAGTCAGC ATCCCATTT ATTACTTAGAC TATGGGAACA CCCCCATGAG TTTTATGGGA 2077

TCTCAAAAAC AAATAACTG ATTTCTATTCA ACTTTTGCAA AGGTGGTAT CAATGACCGC TGGTGATGAT 2137

ACGCCAACTG TTGCCTTGC TCGATAATGGT AAGGTGGTAT CAATGACCGC TGGTGATGAT 2137

ACCACTTTAT CTGATTTAC AACAGATTACT GCTGATTACA ATAATCAGTA GTCACCTGGT 2197

TAATATGGTT TTGTAACCA ATGTAAAAGGC GATGGATCTT TGAAATCGTC TTTTTTTATG 2257
```

FIG. 4F

FIG. 4G  ORF3

```
CACAAATTTT AAAGATCGG TGGTTTGCTT ATG TGG ACT CAA AAA TGG CAC AAA    2311
                                Met Trp Thr Gln Lys Trp His Lys
                                 1                   5

TAT TAT ACA GCA CAA GTT GAT GAA AAT GAC TGT GGT TTA GCT GCA CTA    2359
Tyr Tyr Thr Ala Gln Val Asp Glu Asn Asp Cys Gly Leu Ala Ala Leu
         10                  15                  20

AAT ATG ATC CTA AAA TAC TAT GGC TCC GAT TAC ATG TTG GCC CAT CTT    2407
Asn Met Ile Leu Lys Tyr Tyr Gly Ser Asp Tyr Met Leu Ala His Leu
 25                  30                  35                  40

CGA CAG CTT GCC AAA ACA ACT GCT GAC GGT ACA ACT GTT TTG GGG CTT    2455
Arg Gln Leu Ala Lys Thr Thr Ala Asp Gly Thr Thr Val Leu Gly Leu
                 45                  50                  55

GTT AAA GCA GCA AAA CAC TTA AAT GCC GAA GCT GTG CGT GCT            2503
Val Lys Ala Ala Lys His Leu Asn Ala Glu Ala Val Arg Ala
             60                  65                  70

GAT ATG GAT GCT TTG ACA GCC TCA CAA TTG CCA TTA CCA GTC ATT GTT    2551
Asp Met Asp Ala Leu Thr Ala Ser Gln Leu Pro Leu Pro Val Ile Val
         75                  80                  85
```

```
CAT GTA TTC AAG AAA AAT AAG TTA CCA CAC TAC TAT GTT GTC TAT CAG    2599
His Val Phe Lys Lys Asn Lys Leu Pro His Tyr Tyr Val Val Tyr Gln
 90                      95                     100

GTA ACT GAA AAC GAT TTA ATT ATT GGT GAT CCT GAT CCA ACC GTT AAA    2647
Val Thr Glu Asn Asp Leu Ile Ile Gly Asp Pro Asp Pro Thr Val Lys
105                     110                     115         120

ACC ACT AAA ATA TCG AAA TCA CAA TTT GCT AAA GAA TGG ACC CAG ATT    2695
Thr Thr Lys Ile Ser Lys Ser Gln Phe Ala Lys Glu Trp Thr Gln Ile
                125                     130                     135

GCA ATT ATC ATA GCC CCA ACA GTT AAA TAT AAA CCC ATA AAA GAA TCA    2743
Ala Ile Ile Ile Ala Pro Thr Val Lys Tyr Lys Pro Ile Lys Glu Ser
        140                     145                     150

CGG CAC ACA TTA ATT GAT CTA GTG CCT TTA TTG ATT AAA CAA AAA AGA    2791
Arg His Thr Leu Ile Asp Leu Val Pro Leu Leu Ile Lys Gln Lys Arg
155                     160                     165
```

FIG. 4H

FIG. 4I

```
TTA ATT GGA CTA ATT ATT ACC GCA GCT ATA ACA TTA ATC AGT      2839
Leu Ile Gly Leu Ile Ile Thr Ala Ala Ile Thr Leu Ile Ser
170                 175                 180

ATT GCT GGT GCA TAT TTC TTT CAG TTA ATT ATC GAT ACT TAT TTG CCG   2887
Ile Ala Gly Ala Tyr Phe Phe Gln Leu Ile Ile Asp Thr Tyr Leu Pro
185                 190                 195                 200

CAC TTG ATG ACT AAT AGG CTT TCA CTA GTT GCC ATT GGT CTG ATT GTA   2935
His Leu Met Thr Asn Arg Leu Ser Leu Val Ala Ile Gly Leu Ile Val
                205                 210                 215

GCT TAT GCT TTC CAA GCA ATT ATC AAC TAT ATA CAA AGT TTT TTT ACG   2983
Ala Tyr Ala Phe Gln Ala Ile Ile Asn Tyr Ile Gln Ser Phe Phe Thr
            220                 225                 230

ATT GTA TTA GGA CAA CGT CTC ATG ATC GAC ATC GTT TTA AAA TAC GTT   3031
Ile Val Leu Gly Gln Arg Leu Met Ile Asp Ile Val Leu Lys Tyr Val
        235                 240                 245
```

```
CAC CAT CTT TTT GAT TTA CCA ATG AAT TTT ACT ACC CGT CAT GTC    3079
His His Leu Phe Asp Leu Pro Met Asn Phe Thr Thr Arg His Val
250                 255                 260

GGT GAA ATG ACC TCA CGC TTT TCT GAT GCA AAA ATT ATT GAT GCA    3127
Gly Glu Met Thr Ser Arg Phe Ser Asp Ala Lys Ile Ile Asp Ala
265                 270                 275                 280

CTT GGA AGT ACA ACG CTC ACC CTT TTA GAC ATG TGG ATT TTA TTA    3175
Leu Gly Ser Thr Thr Leu Thr Leu Phe Asp Met Trp Ile Leu Leu
        285                 290                 295

GCA GTA GGG TTA TTT TTG GCC TAT CAA AAC ATC AAT TTA TTT TGC    3223
Ala Val Gly Leu Phe Leu Ala Tyr Gln Asn Ile Asn Leu Phe Cys
            300                 305                 310

TCG TTA GTT GTG GTT CCA ATT TAC ATC TCG ATT GTT TGG CTA TTT AAA    3271
Ser Leu Val Val Val Pro Ile Tyr Ile Ser Ile Val Trp Leu Phe Lys
315                 320                 325
```

FIG. 4J

FIG. 4K

```
AAA ACT TTT AAT CGT TTA AAT CAA GAT ACA ATG GAA AGC AAT GCA GTT    3319
Lys Thr Phe Asn Arg Leu Asn Gln Asp Thr Met Glu Ser Asn Ala Val
330                 335                 340

CTT AAT TCT GCT ATT ATT GAA AGT CTC AGT GGC ATA GAA ACC ATT AAA    3367
Leu Asn Ser Ala Ile Ile Glu Ser Leu Ser Gly Ile Glu Thr Ile Lys
345                 350                 355                 360

TCA CTA ACT GGT GAA GCA ACT ACA AAA AAG ATT GAC ACA CTA TTT        3415
Ser Leu Thr Gly Glu Ala Thr Thr Lys Lys Ile Asp Thr Leu Phe
            365                 370                 375

TCT GAC TTA TTG CAT AAA AAC TTG GCT TAT CAA AAA GCT GAT CAA GGA    3463
Ser Asp Leu Leu His Lys Asn Leu Ala Tyr Gln Lys Ala Asp Gln Gly
        380                 385                 390

CAA CAA GCT ATC AAA GCA GCT ACT AAA TTA ATC CTA ACT ATT GTT ATC    3511
Gln Gln Ala Ile Lys Ala Ala Thr Lys Leu Ile Leu Thr Ile Val Ile
395                 400                 405

CTT TGG TGG GGT ACT TTT GTT ATG CGA CAC CAA CTG TCT TTA GGT        3559
Leu Trp Trp Gly Thr Phe Val Met Arg His Gln Leu Ser Leu Gly
410                 415                 420
```

```
CAG CTG TTA ACT TAT AAT GCT TTG CTC GCT TAC TTC TTG ACC CCA TTA    3607
Gln Leu Leu Thr Tyr Asn Ala Leu Leu Ala Tyr Phe Leu Thr Pro Leu
425                         430                 435             440

GAA AAT ATT ATT AAT TTA CAG CCT AAA CTA CAA GCT GCC AGA GTG GCT    3655
Glu Asn Ile Ile Asn Leu Gln Pro Lys Leu Gln Ala Ala Arg Val Ala
            445                 450                 455

AAT AAT CGA TTA AAT GAG GTT TAT CTA GTA GAG TCT GAA TTT TCT AAA    3703
Asn Asn Arg Leu Asn Glu Val Tyr Leu Val Glu Ser Glu Phe Ser Lys
        460                 465                 470

TCT AGG GAA ATA ACT GCT CTA GAG CAA CTA AAT GGT GAT ATT GAG GTT    3751
Ser Arg Glu Ile Thr Ala Leu Glu Gln Leu Asn Gly Asp Ile Glu Val
475                 480                 485

AAT CAT GTT AGT TTT AAC TAT GGC TAT TGT TCT AAT ATA CTT GAG GAT    3799
Asn His Val Ser Phe Asn Tyr Gly Tyr Cys Ser Asn Ile Leu Glu Asp
490                 495                 500
```

FIG. 4L

FIG. 4M

```
GTT TCT CTA ACA ATT CCA CAT CAT CAG AAG ATT ACT ATT GTA GGC ATG    3847
Val Ser Leu Thr Ile Pro His His Gln Lys Ile Thr Ile Val Gly Met
505                     510                     515                 520

AGT GGT TCG GGG AAA ACG ACC CTA GCC AAG TTG CTA GTT GGT TTT TTT    3895
Ser Gly Ser Gly Lys Thr Thr Leu Ala Lys Leu Leu Val Gly Phe Phe
        525                     530                     535

GAG CCT CAA GAA CAG CAC GGT GAA ATT CAG ATT AAT CAT CAC AAT ATA    3943
Glu Pro Gln Glu Gln His Gly Glu Ile Gln Ile Asn His His Asn Ile
540                     545                     550

TCT GAT ATT AGT CGC ACA ATT TTA CGC CAA TAT ATT AAT TAT GTT CCT    3991
Ser Asp Ile Ser Arg Thr Ile Leu Arg Gln Tyr Ile Asn Tyr Val Pro
555                     560                     565

CAA GAA CCT TTC ATT TTT TCG GGC TCT GTA TTA GAA AAT TTA TTG TTA    4039
Gln Glu Pro Phe Ile Phe Ser Gly Ser Val Leu Glu Asn Leu Leu Leu
570                     575                     580
```

```
GGT AGC CGT CCT GGA GTA ACT CAA CAA ATG ATT GAT CAA GCT TGT TCC   4087
Gly Ser Arg Pro Gly Val Thr Gln Gln Met Ile Asp Gln Ala Cys Ser
585                 590                 595                 600

TTT GCT GAA ATC AAA ACT GAT ATA GAA AAT TTG CCT CAA GGT TAT CAT   4135
Phe Ala Glu Ile Lys Thr Asp Ile Glu Asn Leu Pro Gln Gly Tyr His
            605                 610                 615

ACT AGA TTA AGT GAA AGT GGA TTC AAC TTA TCT GGT GGG CAA AAA CAG   4183
Thr Arg Leu Ser Glu Ser Gly Phe Asn Leu Ser Gly Gly Gln Lys Gln
                620                 625                 630

CGG TTA TCA ATA GCT AGA GCA TTA TTG TCT CCG GCA CAA TGT TTC ATT   4231
Arg Leu Ser Ile Ala Arg Ala Leu Leu Ser Pro Ala Gln Cys Phe Ile
                635                 640                 645

TTT GAC GAA TCA ACC AGT AAT TTA GAC ACC ATT ACT GAA CAT AAA ATA   4279
Phe Asp Glu Ser Thr Ser Asn Leu Asp Thr Ile Thr Glu His Lys Ile
            650                 655                 660
```

FIG. 4N

FIG. 40

```
GTC TCT AAG CTA TTA TTC ATG AAA GAC AAA ACG ATA ATT TTT GTA GCA    4327
Val Ser Lys Leu Leu Phe Met Lys Asp Lys Thr Ile Ile Phe Val Ala
665                      670                     675            680

CAT CGT CTC AAT ATT GCG TCT CAA ACC GAT AAA GTT GTC GTT CTT GAT    4375
His Arg Leu Asn Ile Ala Ser Gln Thr Asp Lys Val Val Val Leu Asp
                685                     690                    695

CAT GGA AAG ATT GTT GAA CAG GGA TCA CAT CGA CAA TTG TTA AAT TAT    4423
His Gly Lys Ile Val Glu Gln Gly Ser His Arg Gln Leu Leu Asn Tyr
            700                     705                    710
                                                            *

AAT GGG TAT TAT GCA CGG TTA ATT CAT AAT CAA GAA TAG CCTGACAAG      4471
Asn Gly Tyr Tyr Ala Arg Leu Ile His Asn Gln Glu
        715                     720

AACCAGTCTG CTATTGATAG ACTATTCTTG TCCGTGAAAT CCTCGCGTAT TTCCGTGAGG  4531

AGCATAGTAT ATTTAGCGAT CTTCAAATTT TAAGTATATATT GATTCATATG TTTATCCTCC 4591
```

```
TAAGTTTGAG GACAAACCGG TACATGTTAT AATACTTCTA CCGGCTTGTC CGGTGTCTGG 4651

AGCATTACCA CATCCTTTCT GGGATAGAGG TAATGCTCTT CTAAAGTGCG CTTAAATAAC 4711

CATTGCCAGT GGTTAATCAG TGCTTTAACA TGTTGCCGTAA GTCATTGAGG GTGTCGGATT 4771

CCACGGCCTC AATGACTTTT TTTGTGCCTT ATAATTAAAG GTGTTAAAAT ACGTCGTAAC 4831

TTACCACCAT AAAGCAGTCC AATTAATTTA TTGACTTCTA AGTAAAATAC CAGGAGTTTT 4891

GCTATGAGTT AACTATGATC CTGGGTGGTC ACTAAAACAT TCCTTAATTC AGGGTCTATA 4951

ACTATCAAAT CGCCCCTCAA AATCATTGTT AAAATAACCC CCAATATCTA TAATGTAGAT 5011

GTTGGGGGTT ATTTATTTTA ATATTAAATA AATAACTTCT TCTATTTGTC ATCAATACTA 5071

AACAATAATT TGTACAAAGT GATTATTTCT TCTAGTTCTT CACGCGATAC ATGATCGACA 5131
```

FIG. 4P

```
ATAGTTTCAT CAGTGACATG TCTTGCCCGT AAATCTAAGG CTATGGTTTG ATCTAATAAT 5191
ACTTTTCCAT ATACTGTTTG ACTACTAGTT AGTCGATGAT ACATTGGAAA ATTACGCTTG 5251
GTACTGCTAA TTGGAGCCGC AATCGTCATG TTACTTGTCT GACAGACTAG ATCATTGCTT 5311
AGCGCAATGG CTGGTCGCTT ATTCATCTGT TCATGACCAC GGCTTGGATT AAAGTTAACA 5371
TAAAATATAT CACCTTGGCT TACCATTGAA GTTCATTACC TTCTGACTTT CCCCAATCAA 5431
GCTCGTGATC CCTTTTCCCG TCATCTTGCC AATCCTTAAA TAGTTCGTGA ATATTGGTTG 5491
GGTTCTTTTT TATTGGTGTT AAAACAATTG ATCCATTTTC AATGGTTATT GTCATATCTT 5551
                                                    EcoRI
GGTTATCATC TAATTTCAGT TGTTTAATAA TTTGGCTAGG AATTC        5596
```

FIG. 4Q

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 5595
      ( B ) TYPE: Nucleic Acid
      ( C ) STRANDEDNESS: Single
      ( D ) TOPOLOGY: Linear ( i i ) MOLECULE TYPE: Plasmid DNA ( i i i ) HYPOTHETICAL: No ( i v ) ANTI-SENSE: No ( v ) FRAGMENT TYPE: N-terminal, internal and C-terminal fragments ( v i ) ORIGINAL SOURCE:
      ( A ) ORGANISM: Pediococcus acidilactici
      ( B ) STRAIN: NRRL-B-18050
      ( C ) INDIVIDUAL ISOLATE: PAC1.0
      ( D ) DEVELOPMENTAL STAGE: N/A
      ( E ) HAPLOTYPE: N/A
      ( F ) TISSUE TYPE: N/A
      ( G ) CELL TYPE: N/A
      ( H ) CELL LINE: N/A
      ( I ) ORGANELLE: N/A ( v i i ) IMMEDIATE SOURCE: N/A ( v i i i ) POSITION IN GENOME: N/A ( i x ) FEATURE:
      ( A ) NAME/KEY: bacteriocin encoding DNA
      ( B ) LOCATION: ECORI to SalI -continued DNA fragment 5.6 kbp.
( C ) IDENTIFICATION METHOD: sequencing
( D ) OTHER INFORMATION: DNA needed for bacteriocin expression.

( x ) PUBLICATION INFORMATION: N/A ( x i ) SEQUENCE DESCRIPTION: SEQ ID NO:1:

```
GTCGACCGGA AATGATCTTT TTAACATCCA AGATAAAGAA AGCAAAATAG CTAAACAGAA      60
GATTGTTAAA TCTGGTAGTA ATAAAGATGG CATACACACA AATAGAGCTA TTAAACGCTG     120
GTGGAAATTC TGGTAAAAGT TAATGTAAGC CTTAAGGTTT CAACTAAAGC AATTACAGTC     180
AACCATAACC ATAGTATTGG ATTGTCATTT TATTGGCTAT AAAATAGTAA ATCAGTGAAT     240
TTCATTACAA AAGGGCTCAC AAAAAATTGT TTTCTTCCTC CAACAATAGC GAGACGCTTT     300
TCTAATTGCT TGACCCAAAG AGCAATAGAA TATTTGAAG GTCCAATTA TTCTGTTAAT       360
GATTTAAGTG AACGGCCTTC TTGGTGAAAT TTAACCAATG AATCTTTGAA ATCTTGTGAA     420
TAACGAATTG ACATAAAAAT GCTCCTATAT TTTCATTTTA CGGACTGAAT AAAAATAGTC     480
CATTTTTTA GTATAAGAGC AGTAAAACCA GACGTGGAAA CCACGTGGTC TTTTAGTTGA      540
TTCAGTAAAA GAAGCCGAAA CCAACGTTTT CACGTTGGTT TCGGCTTCTT TGGCTTTTAA     600
TTGCGGGAAC GCACACAAAG AGCCAAAAAA GATTTGATAA AATCAAAGCT AGAAACTAGC     660
TCCGGTCATG CTTGTTGCGA TCATTATCGC GTAAGTCTTC TACGTGGGCA TCACCACTCG     720
TATCGATATC TAGTTCTTCG CGGCCGACGT TTTCACTTAC TTGTTTCATA TCTTCGTGTT     780
CTTGTTTACG AATGTTAACT TCTTCTCGAA CGACCGGGCG TTTGTTGACA TCGGTAGTTG     840
CAGCCGCACC ATCTCCGGGC TTTCTTTCGA TCACGATTTC TTCTCGTTTA AAATGAATAT     900
ATAAACTGTG TCATAACTTA AAAGATACTG CGTTGATAGC CAGGTTTCAA AAATTGACCA     960
AGATCGTTAA CCAGTTTTGG TGCGAAAATA TCTAACTAAT ACTTGACATT TAAATTGAGT    1020
GGGAACTAGA ATAAGCGCGT ATTAAGGATA ATTTAAGAAG AAGGAGATTT TTGTG ATG    1078
                                                                Met
```

```
AAA AAA ATT GAA AAA TTA ACT GAA AAA GAA ATG GCC AAT ATC ATT GGT   1126
Lys Lys Ile Glu Lys Leu Thr Glu Lys Glu Met Ala Asn Ile Ile Gly
        -15              -10              -5
GGT AAA TAC TAC GGT AAT GGG GTT ACT TGT GGC AAA CAT TCC TGC TCT   1174
Gly Lys Tyr Tyr Gly Asn Gly Val Thr Cys Gly Lys His Ser Cys Ser
     1               5                10                 15
GTT GAC TGG GGT AAG GCT ACC ACT TGC ATA ATC AAT AAT GGA GCT ATG   1222
Val Asp Trp Gly Lys Ala Thr Thr Cys Ile Ile Asn Asn Gly Ala Met
              20                 25                  30
GCA TGG GCT ACT GGT GGA CAT CAA GGT AAT CAT AAA TGC                1261
Ala Trp Ala Thr Gly Gly His Gln Gly Asn His Lys Cys
              35                40
```

```
TAGCATTATG CTGAGCTGGC ATCAATAAAG GGGTGATTTT ATG AAT AAG ACT AAG   1316
                                            Met Asn Lys Thr Lys
                                             1               5
TCG GAA CAT ATT AAA CAA CAA GCT TTG GAC TTA TTT ACT AGG CTA CAG   1364
Ser Glu His Ile Lys Gln Gln Ala Leu Asp Leu Phe Thr Arg Leu Gln
              10                 15                  20
TTT TTA CTA CAG AAG CAC GAT ACT ATC GAA CCT TAC CAG TAC GTT TTA   1412
Phe Leu Leu Gln Lys His Asp Thr Ile Glu Pro Tyr Gln Tyr Val Leu
             25                  30                  35
GAT ATT CTG GAG ACT GGT ATC AGT AAA ACT AAA CAT AAC CAG CAA ACG   1460
Asp Ile Leu Glu Thr Gly Ile Ser Lys Thr Lys His Asn Gln Gln Thr
             40                 45                   50
CCT GAA CGA CAA GCT CGT GTA GTC TAC AAC AAG ATT GCC AGC CAA GCG   1508
Pro Glu Arg Gln Ala Arg Val Val Tyr Asn Lys Ile Ala Ser Gln Ala
         55                60                    65
```

| | | | | | | | | | | | | | | | | |
|---|---|---|---|---|---|---|---|---|---|---|---|---|---|---|---|---|
|TTA|GTA|GAT|AAG|TTA|CAT|TTT|ACT|GCC|GAA|GAA|AAC|AAA|GTT|CTA|GCA|1556|
|Leu|Val|Asp|Lys|Leu|His|Phe|Thr|Ala|Glu|Glu|Asn|Lys|Val|Leu|Ala| |
|70| | | |75| | | |80| | | |  | | |85| |

| | | | | | | | | | | | | | | | | |
|---|---|---|---|---|---|---|---|---|---|---|---|---|---|---|---|---|
|GCC|ATC|AAT|GAA|TTG|GCG|CAT|TCT|CAA|AAA|GGG|TGG|GGC|GAG|TTT|AAC|1604|
|Ala|Ile|Asn|Glu|Leu|Ala|His|Ser|Gln|Lys|Gly|Trp|Gly|Glu|Phe|Asn| |
| | | | | |90| | | |95| | | | |100| | |

| | | | | | | | | | | |
|---|---|---|---|---|---|---|---|---|---|---|
|ATG|CTA|GAT|ACT|ACC|AAT|ACG|TGG|CCT|AGC|CAA|TAGTACTGAT AAAGGGGATA 1657|
|Met|Leu|Asp|Thr|Asn|Thr|Trp|Pro|Ser|Gln| | |
| | | |105| | | |110| | | | |

TTGTAGTTGT CTAAGAAATT TTGGTCAAAT ATCTTTTTAG CATTAGGCGT CTTTCTTGCT 1717

TTTGCAGGAG TTGCTACCAT ATCGGTGAGT GCTGACAGTT CCGCTACTAT AGAATCAAAT 1777

ACTAGCTCGA AAATCATCGA TGGTGCAACT TATGAAGAAA ACATCAGGGG CGTTATTCCT 1837

ATTACGCTAA CTCAATATTT GCATAAAGCT CAAACTGGAG AAAAATTTAT TGTCTTTGTC 1897

GGGTTCAAGG AGTGTGTGCA TTGTCGTAAA TTTTCTCCAG TCATGAAACA GTACTTACAA 1957

CAAAGTCAGC ATCCCATTTA TTACTTAGAC TATGGGAACA ACGGGTCTTT CAGCATGGCT 2017

TCTCAAAAAC AAATAACTGA TTTCTATTCA ACTTTTGCAA CCCCCATGAG TTTTATGGGA 2077

ACGCCAACTG TTGCCTTGCT CGATAATGGT AAGGTGGTAT CAATGACCGC TGGTGATGAT 2137

ACCACTTTAT CTGATTTACA ACAGATTACT GCTGATTACA ATAATCAGTA GTCACCTGGT 2197

TAATATGGTT TTGTAACCAA TGTAAAGGC GATGGATCTT TGAAATCGTC TTTTTTATG 2257

| | | | | | | | | | |
|---|---|---|---|---|---|---|---|---|---|
|CACAAATTTT|AAAGATCGGT|GGTTTGCTT|ATG|TGG|ACT|CAA|AAA|TGG|CAC AAA 2310|
| | | |Met|Trp|Thr|Gln|Lys|Trp|His Lys|
| | | |1| | | |5| | |

| | | | | | | | | | | | | | | | | |
|---|---|---|---|---|---|---|---|---|---|---|---|---|---|---|---|---|
|TAT|TAT|ACA|GCA|CAA|GTT|GAT|GAA|AAT|GAC|TGT|GGT|TTA|GCT|GCA|CTA|2358|
|Tyr|Tyr|Thr|Ala|Gln|Val|Asp|Glu|Asn|Asp|Cys|Gly|Leu|Ala|Ala|Leu| |
| | |10| | | |15| | | |20| | | | | | |

| | | | | | | | | | | | | | | | | |
|---|---|---|---|---|---|---|---|---|---|---|---|---|---|---|---|---|
|AAT|ATG|ATC|CTA|AAA|TAC|TAT|GGC|TCC|GAT|TAC|ATG|TTG|GCC|CAT|CTT|2406|
|Asn|Met|Ile|Leu|Lys|Tyr|Tyr|Gly|Ser|Asp|Tyr|Met|Leu|Ala|His|Leu| |
|25| | | |30| | | |35| | | | | | |40| |

| | | | | | | | | | | | | | | | | |
|---|---|---|---|---|---|---|---|---|---|---|---|---|---|---|---|---|
|CGA|CAG|CTT|GCC|AAA|ACA|ACT|GCT|GAC|GGT|ACA|ACT|GTT|TTG|GGG|CTT|2454|
|Arg|Gln|Leu|Ala|Lys|Thr|Thr|Ala|Asp|Gly|Thr|Thr|Val|Leu|Gly|Leu| |
| | | | |45| | | |50| | | | |55| | | |

| | | | | | | | | | | | | | | | | |
|---|---|---|---|---|---|---|---|---|---|---|---|---|---|---|---|---|
|GTT|AAA|GCA|GCA|AAA|CAC|TTA|AAT|TTA|AAT|GCC|GAA|GCT|GTG|CGT|GCT|2502|
|Val|Lys|Ala|Ala|Lys|His|Leu|Asn|Leu|Asn|Ala|Glu|Ala|Val|Arg|Ala| |
| | | |60| | | |65| | | | |70| | | | |

| | | | | | | | | | | | | | | | | |
|---|---|---|---|---|---|---|---|---|---|---|---|---|---|---|---|---|
|GAT|ATG|GAT|GCT|TTG|ACA|GCC|TCA|CAA|TTG|CCA|TTA|CCA|GTC|ATT|GTT|2550|
|Asp|Met|Asp|Ala|Leu|Thr|Ala|Ser|Gln|Leu|Pro|Leu|Pro|Val|Ile|Val| |
| | |75| | | |80| | | |85| | | | | | |

| | | | | | | | | | | | | | | | | |
|---|---|---|---|---|---|---|---|---|---|---|---|---|---|---|---|---|
|CAT|GTA|TTC|AAG|AAA|AAT|AAG|TTA|CCA|CAC|TAC|TAT|GTT|GTC|TAT|CAG|2598|
|His|Val|Phe|Lys|Lys|Asn|Lys|Leu|Pro|His|Tyr|Tyr|Val|Val|Tyr|Gln| |
|90| | | | |95| | | | |100| | | | | | |

| | | | | | | | | | | | | | | | | |
|---|---|---|---|---|---|---|---|---|---|---|---|---|---|---|---|---|
|GTA|ACT|GAA|AAC|GAT|TTA|ATT|ATT|GGT|GAT|CCT|GAT|CCA|ACC|GTT|AAA|2646|
|Val|Thr|Glu|Asn|Asp|Leu|Ile|Ile|Gly|Asp|Pro|Asp|Pro|Thr|Val|Lys| |
|105| | | |110| | | | |115| | | | | |120| |

| | | | | | | | | | | | | | | | | |
|---|---|---|---|---|---|---|---|---|---|---|---|---|---|---|---|---|
|ACC|ACT|AAA|ATA|TCG|AAA|TCA|CAA|TTT|GCT|AAA|GAA|TGG|ACC|CAG|ATT|2694|
|Thr|Thr|Lys|Ile|Ser|Lys|Ser|Gln|Phe|Ala|Lys|Glu|Trp|Thr|Gln|Ile| |
| | | | |125| | | |130| | | | |135| | | |

| | | | | | | | | | | | | | | | | |
|---|---|---|---|---|---|---|---|---|---|---|---|---|---|---|---|---|
|GCA|ATT|ATC|ATA|GCC|CCA|ACA|GTT|AAA|TAT|AAA|CCC|ATA|AAA|GAA|TCA|2742|
|Ala|Ile|Ile|Ile|Ala|Pro|Thr|Val|Lys|Tyr|Lys|Pro|Ile|Lys|Glu|Ser| |
| | | |140| | | |145| | | | |150| | | | |

| | | | | | | | | | | | | | | | | |
|---|---|---|---|---|---|---|---|---|---|---|---|---|---|---|---|---|
|CGG|CAC|ACA|TTA|ATT|GAT|CTA|GTG|CCT|TTA|TTG|ATT|AAA|CAA|AAA|AGA|2790|
|Arg|His|Thr|Leu|Ile|Asp|Leu|Val|Pro|Leu|Leu|Ile|Lys|Gln|Lys|Arg| |
| | |155| | | |160| | | | |165| | | | | |

| | | | | | | | | | | | | | | | | |
|---|---|---|---|---|---|---|---|---|---|---|---|---|---|---|---|---|
|TTA|ATT|GGA|CTA|ATT|ATT|ACC|GCA|GCA|GCT|ATA|ACA|ACA|TTA|ATC|AGT|2838|
|Leu|Ile|Gly|Leu|Ile|Ile|Thr|Ala|Ala|Ala|Ile|Thr|Thr|Leu|Ile|Ser| |
|170| | | | |175| | | | |180| | | | | | |

| | | | | | | | | | | | | | | | | |
|---|---|---|---|---|---|---|---|---|---|---|---|---|---|---|---|---|
|ATT|GCT|GGT|GCA|TAT|TTC|TTT|CAG|TTA|ATT|ATC|GAT|ACT|TAT|TTG|CCG|2886|

```
Ile Ala Gly Ala Tyr Phe Phe Gln Leu Ile Ile Asp Thr Tyr Leu Pro
185             190                 195                 200

CAC TTG ATG ACT AAT AGG CTT TCA CTA GTT GCC ATT GGT CTG ATT GTA    2934
His Leu Met Thr Asn Arg Leu Ser Leu Val Ala Ile Gly Leu Ile Val
                205                 210                 215

GCT TAT GCT TTC CAA GCA ATT ATC AAC TAT ATA CAA AGT TTT TTT ACG    2982
Ala Tyr Ala Phe Gln Ala Ile Ile Asn Tyr Ile Gln Ser Phe Phe Thr
            220                 225                 230

ATT GTA TTA GGA CAA CGT CTC ATG ATC GAC ATC GTT TTA AAA TAC GTT    3030
Ile Val Leu Gly Gln Arg Leu Met Ile Asp Ile Val Leu Lys Tyr Val
        235                 240                 245

CAC CAT CTT TTT GAT TTA CCA ATG AAT TTT TTT ACT ACC CGT CAT GTC    3078
His His Leu Phe Asp Leu Pro Met Asn Phe Phe Thr Thr Arg His Val
250                 255                 260

GGT GAA ATG ACC TCA CGC TTT TCT GAT GCA AGC AAA ATT ATT GAT GCA    3126
Gly Glu Met Thr Ser Arg Phe Ser Asp Ala Ser Lys Ile Ile Asp Ala
265                 270                 275                 280

CTT GGA AGT ACA ACG CTC ACC CTT TTT TTA GAC ATG TGG ATT TTA TTA    3174
Leu Gly Ser Thr Thr Leu Thr Leu Phe Leu Asp Met Trp Ile Leu Leu
                285                 290                 295

GCA GTA GGG TTA TTT TTG GCC TAT CAA AAC ATC AAT TTA TTT TTA TGC    3222
Ala Val Gly Leu Phe Leu Ala Tyr Gln Asn Ile Asn Leu Phe Leu Cys
            300                 305                 310

TCG TTA GTT GTG GTT CCA ATT TAC ATC TCG ATT GTT TGG CTA TTT AAA    3270
Ser Leu Val Val Val Pro Ile Tyr Ile Ser Ile Val Trp Leu Phe Lys
        315                 320                 325

AAA ACT TTT AAT CGT TTA AAT CAA GAT ACA ATG GAA AGC AAT GCA GTT    3318
Lys Thr Phe Asn Arg Leu Asn Gln Asp Thr Met Glu Ser Asn Ala Val
330                 335                 340

CTT AAT TCT GCT ATT ATT GAA AGT CTC AGT GGC ATA GAA ACC ATT AAA    3366
Leu Asn Ser Ala Ile Ile Glu Ser Leu Ser Gly Ile Glu Thr Ile Lys
345                 350                 355                 360

TCA CTA ACT GGT GAA GCA ACT ACA AAA AAA AAG ATT GAC ACA CTA TTT    3414
Ser Leu Thr Gly Glu Ala Thr Thr Lys Lys Lys Ile Asp Thr Leu Phe
                365                 370                 375

TCT GAC TTA TTG CAT AAA AAC TTG GCT TAT CAA AAA GCT GAT CAA GGA    3462
Ser Asp Leu Leu His Lys Asn Leu Ala Tyr Gln Lys Ala Asp Gln Gly
            380                 385                 390

CAA CAA GCT ATC AAA GCA GCT ACT AAA TTA ATC CTA ACT ATT GTT ATC    3510
Gln Gln Ala Ile Lys Ala Ala Thr Lys Leu Ile Leu Thr Ile Val Ile
        395                 400                 405

CTT TGG TGG GGT ACT TTT TTT GTT ATG CGA CAC CAA CTG TCT TTA GGT    3558
Leu Trp Trp Gly Thr Phe Phe Val Met Arg His Gln Leu Ser Leu Gly
410                 415                 420

CAG CTG TTA ACT TAT AAT GCT TTG CTC GCT TAC TTC TTG ACC CCA TTA    3606
Gln Leu Leu Thr Tyr Asn Ala Leu Leu Ala Tyr Phe Leu Thr Pro Leu
425                 430                 435                 440

GAA AAT ATT ATT AAT TTA CAG CCT AAA CTA CAA GCT GCC AGA GTG GCT    3654
Glu Asn Ile Ile Asn Leu Gln Pro Lys Leu Gln Ala Ala Arg Val Ala
                445                 450                 455

AAT AAT CGA TTA AAT GAG GTT TAT CTA GTA GAG TCT GAA TTT TCT AAA    3702
Asn Asn Arg Leu Asn Glu Val Tyr Leu Val Glu Ser Glu Phe Ser Lys
            460                 465                 470

TCT AGG GAA ATA ACT GCT CTA GAG CAA CTA AAT GGT GAT ATT GAG GTT    3750
Ser Arg Glu Ile Thr Ala Leu Glu Gln Leu Asn Gly Asp Ile Glu Val
        475                 480                 485

AAT CAT GTT AGT TTT AAC TAT GGC TAT TGT TCT AAT ATA CTT GAG GAT    3798
Asn His Val Ser Phe Asn Tyr Gly Tyr Cys Ser Asn Ile Leu Glu Asp
490                 495                 500

GTT TCT CTA ACA ATT CCA CAT CAT CAG AAG ATT ACT ATT GTA GGC ATG    3846
Val Ser Leu Thr Ile Pro His His Gln Lys Ile Thr Ile Val Gly Met
505                 510                 515                 520
```

| | | | | | | | | | | | | | | | | |
|---|---|---|---|---|---|---|---|---|---|---|---|---|---|---|---|---|
| AGT | GGT | TCG | GGG | AAA | ACG | ACC | CTA | GCC | AAG | TTG | CTA | GTT | GGT | TTT | TTT | 3894 |
| Ser | Gly | Ser | Gly | Lys<br>525 | Thr | Thr | Leu | Ala | Lys<br>530 | Leu | Leu | Val | Gly | Phe<br>535 | Phe | |
| GAG | CCT | CAA | GAA | CAG | CAC | GGT | GAA | ATT | CAG | ATT | AAT | CAT | CAC | AAT | ATA | 3942 |
| Glu | Pro | Gln | Glu<br>540 | Gln | His | Gly | Glu | Ile<br>545 | Gln | Ile | Asn | His | His<br>550 | Asn | Ile | |
| TCT | GAT | ATT | AGT | CGC | ACA | ATT | TTA | CGC | CAA | TAT | ATT | AAT | TAT | GTT | CCT | 3990 |
| Ser | Asp | Ile<br>555 | Ser | Arg | Thr | Ile | Leu<br>560 | Arg | Gln | Tyr | Ile | Asn<br>565 | Tyr | Val | Pro | |
| CAA | GAA | CCT | TTC | ATT | TTT | TCG | GGC | TCT | GTA | TTA | GAA | AAT | TTA | TTG | TTA | 4038 |
| Gln | Glu<br>570 | Pro | Phe | Ile | Phe | Ser<br>575 | Gly | Ser | Val | Leu | Glu<br>580 | Asn | Leu | Leu | Leu | |
| GGT | AGC | CGT | CCT | GGA | GTA | ACT | CAA | CAA | ATG | ATT | GAT | CAA | GCT | TGT | TCC | 4086 |
| Gly<br>585 | Ser | Arg | Pro | Gly | Val<br>590 | Thr | Gln | Gln | Met | Ile<br>595 | Asp | Gln | Ala | Cys | Ser<br>600 | |
| TTT | GCT | GAA | ATC | AAA | ACT | GAT | ATA | GAA | AAT | TTG | CCT | CAA | GGT | TAT | CAT | 4134 |
| Phe | Ala | Glu | Ile | Lys<br>605 | Thr | Asp | Ile | Glu | Asn<br>610 | Leu | Pro | Gln | Gly | Tyr<br>615 | His | |
| ACT | AGA | TTA | AGT | GAA | AGT | GGA | TTC | AAC | TTA | TCT | GGT | GGG | CAA | AAA | CAG | 4182 |
| Thr | Arg | Leu | Ser<br>620 | Glu | Ser | Gly | Phe | Asn<br>625 | Leu | Ser | Gly | Gly | Gln<br>630 | Lys | Gln | |
| CGG | TTA | TCA | ATA | GCT | AGA | GCA | TTA | TTG | TCT | CCG | GCA | CAA | TGT | TTC | ATT | 4230 |
| Arg | Leu | Ser<br>635 | Ile | Ala | Arg | Ala | Leu<br>640 | Leu | Ser | Pro | Ala | Gln<br>645 | Cys | Phe | Ile | |
| TTT | GAC | GAA | TCA | ACC | AGT | AAT | TTA | GAC | ACC | ATT | ACT | GAA | CAT | AAA | ATA | 4278 |
| Phe | Asp | Glu<br>650 | Ser | Thr | Ser | Asn<br>655 | Leu | Asp | Thr | Ile | Thr<br>660 | Glu | His | Lys | Ile | |
| GTC | TCT | AAG | CTA | TTA | TTC | ATG | AAA | GAC | AAA | ACG | ATA | ATT | TTT | GTA | GCA | 4326 |
| Val<br>665 | Ser | Lys | Leu | Leu | Phe<br>670 | Met | Lys | Asp | Lys | Thr<br>675 | Ile | Ile | Phe | Val | Ala<br>680 | |
| CAT | CGT | CTC | AAT | ATT | GCG | TCT | CAA | ACC | GAT | AAA | GTT | GTC | GTT | CTT | GAT | 4374 |
| His | Arg | Leu | Asn | Ile<br>685 | Ala | Ser | Gln | Thr | Asp<br>690 | Lys | Val | Val | Val | Leu<br>695 | Asp | |
| CAT | GGA | AAG | ATT | GTT | GAA | CAG | GGA | TCA | CAT | CGA | CAA | TTG | TTA | AAT | TAT | 4422 |
| His | Gly | Lys | Ile<br>700 | Val | Glu | Gln | Gly | Ser<br>705 | His | Arg | Gln | Leu | Leu<br>710 | Asn | Tyr | |
| AAT | GGG | TAT | TAT | GCA | CGG | TTA | ATT | CAT | AAT | CAA | GAA | TAGCCT | GACAAGAACC | | | 4474 |
| Asn | Gly | Tyr<br>715 | Tyr | Ala | Arg | Leu | Ile | His | Asn<br>720 | Gln | Glu | | | | | |

```
AGTCTGCTAT TGATAGACTA TTCTTGTCCG TGAAATCCTC GCGTATTTCC GTGAGGAGCA  4534
TAGTATATTT AGCGATCTTC AAATTTTAAG TATATTGATT CATATGTTTA TCCTCCTAAG  4594
TTTGAGGACA AACCGGTACA TGTTATAATA CTTCTACCGG CTTGTCCGGT GTCTGGAGCA  4654
TTACCACATC CTTTCTGGGA TAGAGGTAAT GCTCTTCTAA AGTGCGCTTA ATAACCATT   4714
GCCAGTGGTT AATCAGTGCT TTAACATGTT GCGTAAGTCA TTGAGGGTGT CGGATTCCAC  4774
GGCCTCAATG ACTTTTTTTG TGCCTTATAA TTAAAGGTGT TAAAATACGT CGTAACTTAC  4834
CACCATAAAG CAGTCCAATT AATTTATTGA CTTCTAAGTA AAATACCAGG AGTTTTGCTA  4894
TGAGTTAACT ATGATCCTGG GTGGTCACTA AAACATTCCT TAATTCAGGG TCTATAACTA  4954
TCAAATCGCC CCTCAAAATC ATTGTTAAAA TAACCCCCAA TATCTATAAT GTAGATGTTG  5014
GGGGTTATTT ATTTTAATAT TAAATAAATA ACTTCTTCTA TTTGTCATCA ATACTAAACA  5074
ATAATTTGTA CAAAGTGATT ATTTCTTCTA GTTCTTCACG CGATACATGA TCGACAATAG  5134
TTTCATCAGT GACATGTCTT GCCCGTAAAT CTAAGGCTAT GGTTTGATCT AATAATACTT  5194
TTCCATATAC TGTTTGACTA CTAGTTAGTC GATGATACAT TGGAAAATTA CGCTTGGTAC  5254
TGCTAATTGG AGCCGCAATC GTCATGTTAC TTGTCTGACA GACTAGATCA TTGCTTAGCG  5314
CAATGGCTGG TCGCTTATTC ATCTGTTCAT GACCACGGCT TGGATTAAAG TTAACATAAA  5374
```

```
ATATATCACC TTGGCTTACC ATTGAAGTTC ATTACCTTCT GACTTTCCCC AATCAAGCTC  5434

GTGATCCCTT TTCCCGTCAT CTTGCCAATC CTTAAATAGT TCGTGAATAT TGGTTGGGTT  5494

CTTTTTTATT GGTGTTAAAA CAATTGATCC ATTTCAATG  GTTATTGTCA TATCTTGGTT  5554

ATCATCTAAT TTCAGTTGTT TAATAATTTG GCTAGGAATT C                      5595
```

CLONED GENE ENCODING FOR BACTERIOCIN FROM *PEDIOCOCCUS ACIDILACTICI*

CROSS REFERENCE TO RELATED APPLICATIONS

This application is a continuation-in-part of co-pending application Ser. No. 375,344, filed Jul. 3, 1989, abandoned which is a continuation-in-part of Ser. No. 012,619, filed Feb. 9, 1987, now U.S. Pat. No. 4,883,673, and a continuation-in-part of application Ser. No. 514,102, filed Apr. 25, 1990.

BACKGROUND OF THE INVENTION

(1) SUMMARY OF THE INVENTION

The present invention relates to a sequenced gene encoding for a bacteriocin in *Pediococcus acidilactici* and in particular to a gene that is essential for the production of the functional bacteriocin, called hereafter helper protein, and to the cloned gene in a vector which is transformed into a bacterium. In particular, the present invention relates to a sequenced gene encoding for a bacteriocin derived from a plasmid in *Pediococcus acidilactici*.

(2) Prior Art

The pediococci are a diverse group of Gram-positive homofermentative lactic acid bacteria often found as saphrophytes on vegetable material (Gonzalez, C. F., and B. S. Kunka, Appl. Environ. Microbiol. 53:2534-2538 (1987); and Mundt, J. O., W. G. Beattie, and F. R. Wieland, J. Bacteriol. 98:938-942 (1969)). Commercially, pediococci are used in the fermentation of vegetables (Pederson, Bacteriol. Rev. 13:225-232 (1949) and meats (Smith, J. L., and S. A. Palumbo, J. Food Prot. 46:997-1006 (1983)).

Some strains of *P. pentosaceus, P. cerevisiae* and *P. acidilactici* have been found to contain resident plasmids although the roles of most of these remain unknown (Gonzalez, C. F., and B. S. Kunka, Appl. Environ. Microbiol. 46:81-89 (1983); Graham, D. C., and L. L. McKay, Appl. Environ. Microbiol. 50:532-534 (1985); and Raccach, M., CRC Crit. Rev. Microbiol. 14:291-309 (1987)). The association of raffinose fermentation and plasmid DNA has been reported (Gonzalez, C. F., and B. S. Kunka, Appl. Environ. Microbiol. 51:105-109 (1986)), as has the ability of *P. acidilactici* to ferment sucrose (Gonzalez, C. F. and B. S. Kunka, Appl. Environ. Microbiol 53:2534-2538 (1987)). Moreover, there have been several reports which associate the production of bacteriocins with host plasmid DNA (Daeschel, M. A., and T. R. Klaenhammer, Appl. Environ. Microbiol. 51:1538-1541 (1985); Gonzalez, C. F., and B. S. Kunka, Appl. Environ. Microbiol. 53:2534-2538 (1987); Graham, D. C., and L. McKay, Appl. Environ. Microbiol. 50:532-534 (1985); and Bhunia et al, J. Applied Bact. 65:261-268 (1988)). It was shown by Gonzalez, C. F. and B. S. Kunka (Appl. Environ. Microbiol. 53:2534-2538 (1987)) that bacteriocin production was encoded by a 9.0 kbp plasmid pSRQ11 in *P. acidilactici* PAC1.0. Further work (Pucci, M. P., E. R. Vedamuthu, B. S. Kunka and P. A. Vandenbergh, Appl. Environ. Microbiol. 54:2349-2353 (1988)) demonstrated that the bacteriocin of *P. acidilactici* PAC1.0 was active against a wide spectrum of gram positive lactic acid bacteria, and also against *Listeria monocytogenes*. This anti-listerial activity was observed in broth and on agar plates, as well as in some dairy products. Inhibition of *L. monocytogenes* by this bacteriocin, PA-1, has also been noted in fermented semi-dry sausage (Berry, E. D., M. B. Liewen, R. W. Mandigo and R. W. Huthine, J. Food Protection 53, 194-197 (1990)) and fresh meat (Nielsen, J. W., J. S. Dickson and J. D. Crouse, Appl. Environ. Microbiol. 56, 2142-2145 (1990)). The cloning of genes for the production of the bacteriocin has not been described and this would be useful for producing bacteriocin in significant quantities in genera unrelated to Pediococcus, or enhancing production in the pediococci.

Cloned Gram-positive genes for different unrelated proteins have been shown to express in *Escherichia coli* (Gilmore, M. S., Curr. Top. Microbiol. Immunol. 118:219-234 (1985); Rogeson, J. P., R. G. Barletta, and R. Curtiss III, J. Bacteriol. 153:211-221 (1983); and Smorawinska, M., J. C. Hsu, J. B. Hansen, E. K. Jagusztyn-Krynicka, Y. H. Abiko, and R. Curtiss III, J. Bacteriol. 153:1095-1097 (1983)).

OBJECTS

It is therefore an object of the present invention to provide the sequenced gene for the bacteriocin and its essential helper protein(s), which are used as vectors that can be transferred to other microorganisms that contain the genetic information of these genes in such a way that the functional bacteriocin is produced by these new hosts. Such microorganisms are particularly in the genera Lactococcus, Lactobacillus, Leuconostoc, Streptococcus, Pediococcus, richia, Bacillus and yeasts. These and other objects will become increasingly apparent by reference to the following description and the drawings.

IN THE DRAWINGS

FIG. 1 shows a restriction endonuclease site map of pSRQ11. *P. acidilactici* PAC1.0 plasmid pSRQ11 is 9.0 kbp and contains the gene for PA-1 bacteriocin.

FIGS. 2A and 2B show restriction endonuclease site maps of pSRQ11.1 and pSRQ11.2, respectively. Both plasmids are 14.8 kbp and contain erythromycin resistance (ery) genes at the locations indicated. The *E. coli* origin of replication (ori) and the remaining part of the chloramphenicol resistance (cml) gene are shown. Numbered triangles (Δ) indicate areas of each plasmid which had been subsequently deleted.

Figure 3A:
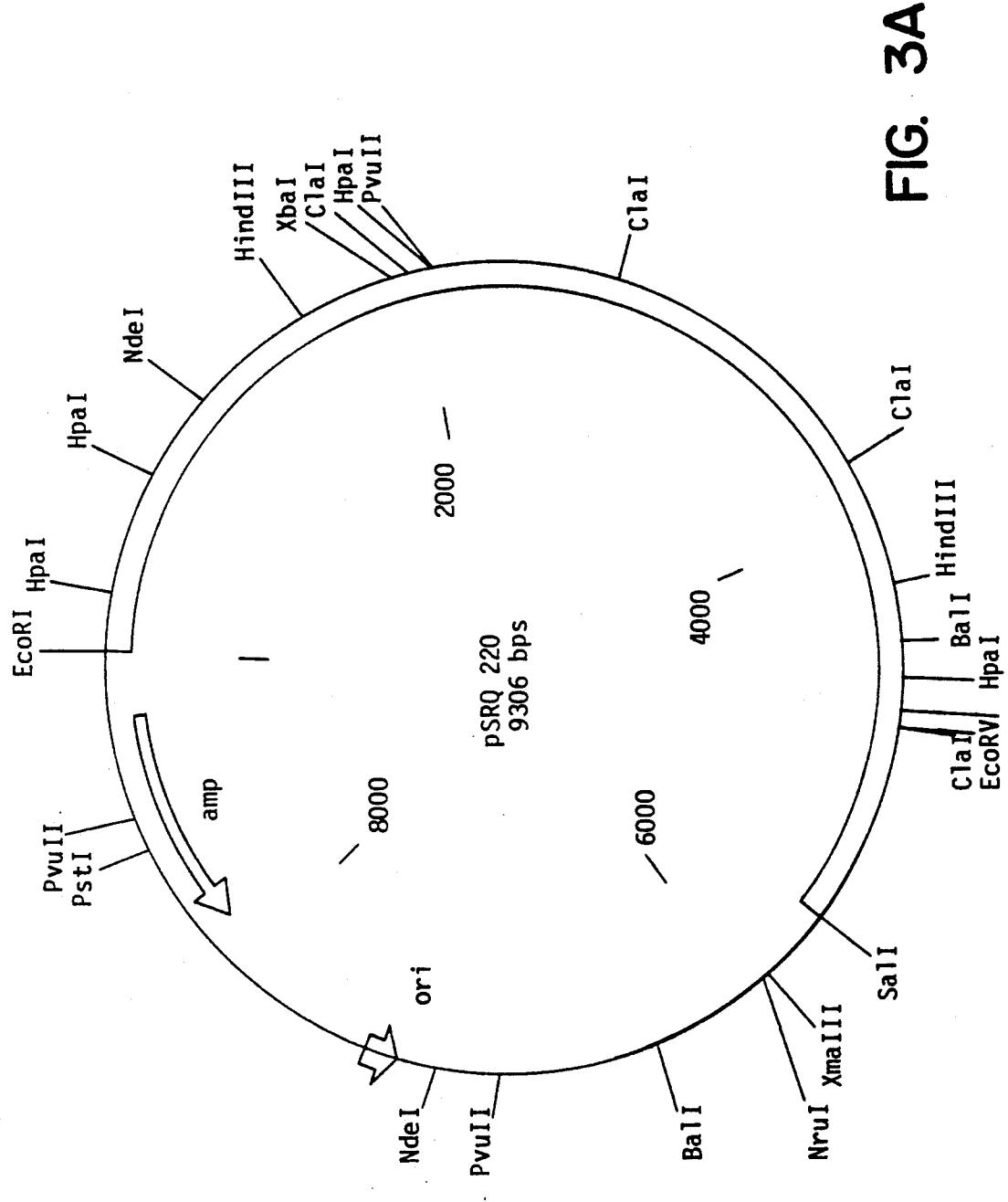

FIG. 3A shows a restriction endonuclease site map of pSRQ220. Plasmid pSRQ220 is 9.3 kbp and is a chimera of *Escherichia coli* plasmid pBR322 and PAC1.0 plasmid pSRQ11 digested with EcoRI and SalI and ligated together. The *Escherichia coli* origin of replication (ori) and the ampicillin resistance (amp) gene are indicated. The 5.6 kbp EcoRI-SalI fragment is indicated by the open box.

Figure 3B:
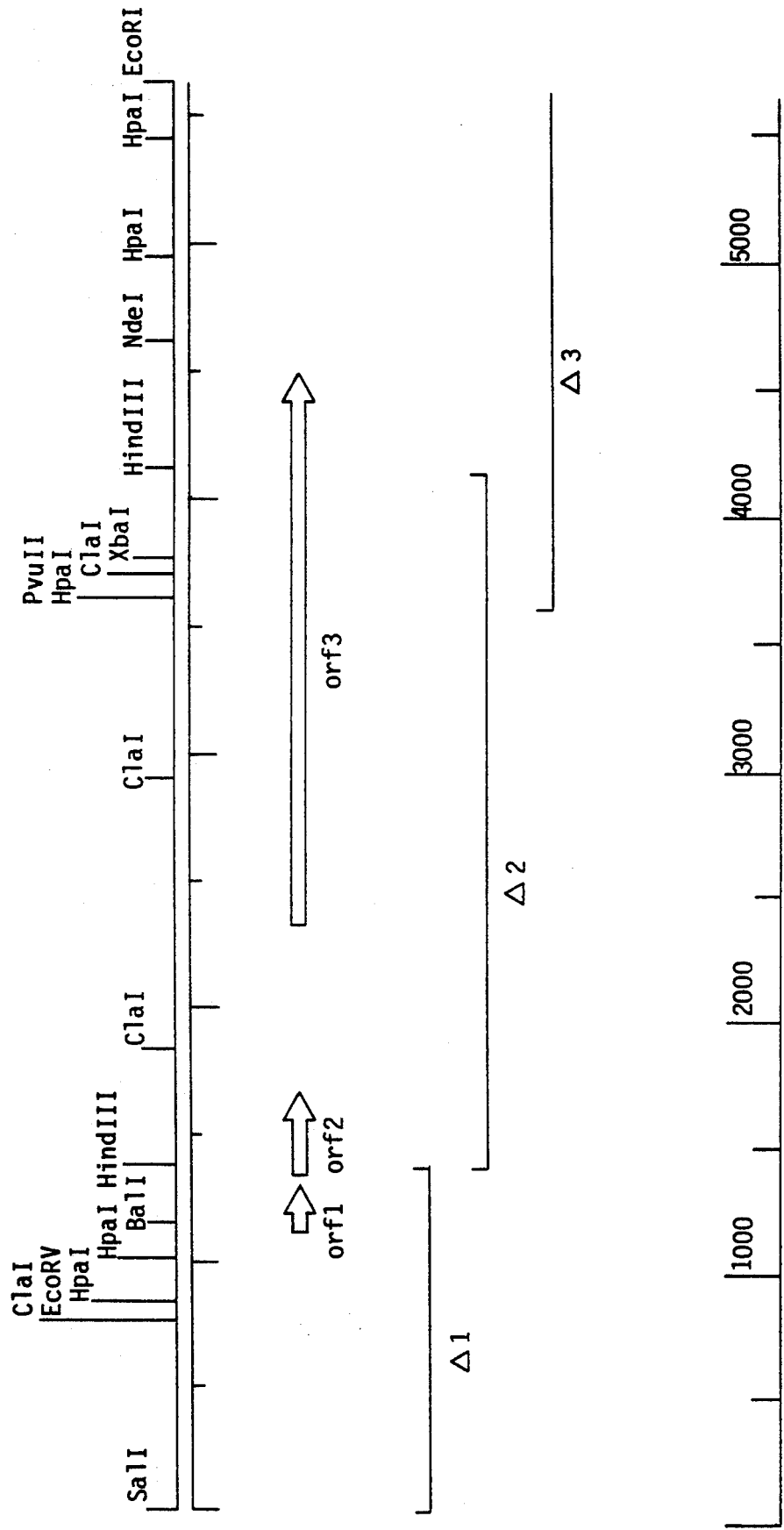

FIG. 3B shows a physical map of the 5.6 kbp EcoRI-SalI fragment from pSRQ220. The horizontal arrows denote open reading frames discussed hereinafter (ORF 1, ORF 2, and ORF 3). The horizontal lines, indicated by numbered triangles (Δ1, Δ2, and Δ3), represent deletions present in plasmids pUR5204 (Δ1), pSRQ220.2 (Δ2), and pSRQ11.13 (Δ3), respectively.

FIGS. 4A to Q shows the nucleotide sequence of the 5.6 kbp EcoRI-SalI insert from pSRQ220. The derived amino acid sequences of ORF1, ORF2, and ORF3 are also shown. The arrow indicates the start of the mature PA-1 bacteriocin. The TAG termination codons are denoted with an asterisk (*).

Figure 5A:
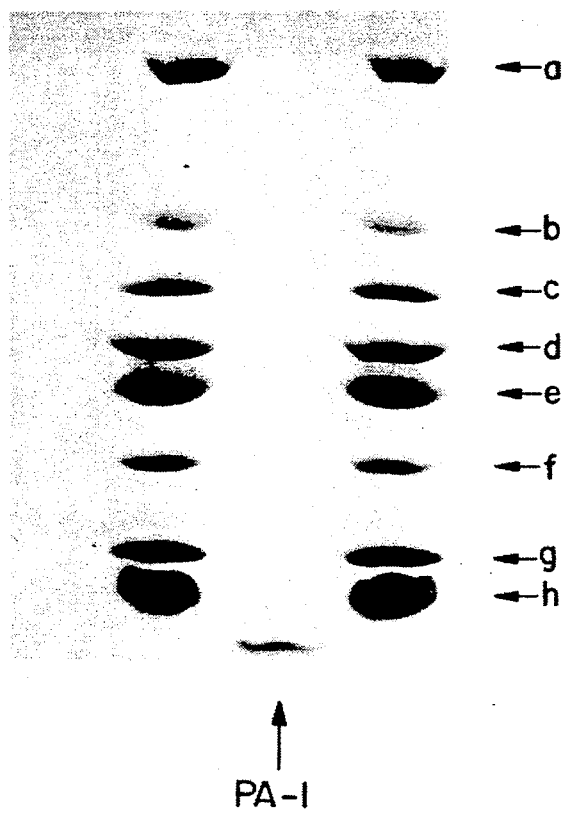

FIG. 5A shows a coomassie staned 5-22% acrylamide SDS-PAGE gel of purified PA-1. a=66000, b=45000, c=36000, d=29000, e=24000, f=20100, g=14200, h=6500 Daltons. Standards a through g are MW-SDS-70L (Sigma), standard h is aprotinin (Sigma).

Figure 5B:
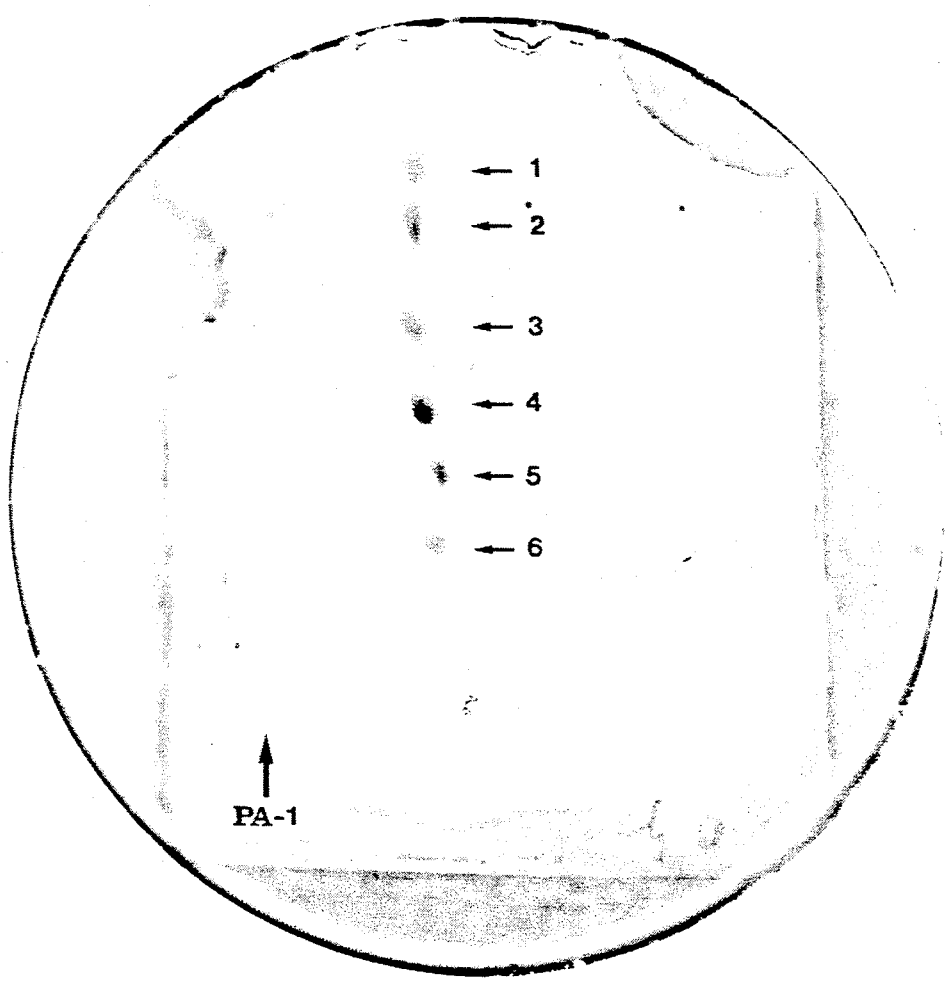

FIG. 5B shows an unstained gel overlayed with a lawn of *Pediococcus pentosaceus* FBB63 indicator cells. Inhibition zone (large arrow) is apparent. 1=110000, 2=84000, 3=47000, 4=33000, 5=24000, 6=16000 Daltons. Prestained standards (Biorad) were used.

GENERAL DESCRIPTION

The present invention relates to a nucleotide sequence as given in FIGS. 4A to Q and derivatives thereof which produces a bacteriocin precursor.

The present invention further relates to a vector containing a nucleotide sequence containing ORF 1 as described in FIGS. 4A to Q maintained in a bacterium in which the nucleotide sequence is preceded by a promoter system and followed by a terminator sequence both functional in the bacterium and express a bacteriocin encoded by the nucleotide sequence in the bacterium.

The nucleotide sequence of the present invention can be maintained in a vector which operates in various bacteria or yeasts. All that is required is that the microorganisms express the bacteriocin.

The DNA encoding the bacteriocin can be replicated by means of a polymerase chain reaction as described in *Chemical Engineering News*, pages 36–46, Oct. 1, 1990 and in other references. The appropriate 3' and 5' terminal regions of the DNA encoding the bacteriocin can be used as primers defining the region to be replicated.

The gene segment is preferably derived from *Pediococcus acidilactici* NRRL-B-18050 also known herein as PAC1.0, which is deposited with the Northern Regional Research Laboratory in Peoria, Ill. under the Budapest Treaty. The genes involved in bacteriocin activity are carried on a 9.0 kbp plasmid designated herein as pSRQ11. A DNA segment (SalI to EcoRI; 5.6 kbp) is ligated in purified form in a vector plasmid pBR322 and called pSRQ220. This plasmid is transformed to *Escherichia coli* NRRL-B-18429 and deposited at the same depository under the Budapest Treaty.

U.S. Pat. No. 4,883,673 which is assigned to a common assignee describes the isolation of a bacteriocin from *Pediococcus acidilactici* NRRL-B-18050 which inhibits various bacteria. A plasmid in this strain was disclosed to encode for the bacteriocin. The bacteriocin was described to be useful in foods to inhibit bacterial spoilage. U.S. Pat. No. 4,929,445, assigned to a common assignee, describes a method of using the bacteriocin to inhibit *Listeria monocytogenes* which produces a severe illness in humans. The plasmid pSRQ11 was described as the source of the bacteriocin. The usefulness of the bacteriocin is well established.

SPECIFIC DESCRIPTION

The following Examples show the steps in sequencing the gene encoding for the bacteriocin.

Bacterial strains and media. The bacterial strains used are listed in Table 1.

TABLE 1

| Strain or plasmid | Remarks[a] | Reference |
|---|---|---|
| *P. acidilactici* | | |
| PAC1.0 | Contains 9.0 kbo PA-1 pediocin plasmid, pSRQ11 | (4) |
| PAC1.14 | PAC1.0 derivative cured of pSRQ11 | (4) |
| *P. pentosaceus* | | |
| FBB63C | Sensitive indicator strain for PA-1 pediocin | (4) |
| *E. coli* | | |
| V850 | Hypersensitivity to macrolide antibiotics | (5) |
| V851 | Tetracycline sensitive | (7) |
| 2g4 | Tetracycline sensitive Ampicillin sensitive | (8) |
| Plasmids | | |
| pBR322 | Ap[r], Tc[r] | (1) |
| pACYC184 | Cm[r], Tc[r] | (2) |
| pVA891 | Em[r] | (6) |
| pSA3 | Em[r], CM[r], Tc[r] | (3) |
| pSRQ11 | 9.0 kbp PA-1 pediocin plasmid | (4) |

[a]Ap, ampicillin; Cm, chloramphenicol; Em, erythromycin; r, resistance, and Tc tetracycline.
(1) Bolivar, F., et al., Gene 2:95–113 (1977).
(2) Chang, A. C. Y., et al., J. Bacteriol. 134:1141–1156 (1978).
(3) Dao, My Lien, et al., Applied and Environmental Microbiology. 49:115–119 (Jan. 1985).
(4) Gonzalez, Carlos F., et al., Applied and Environmental Microbiology. 53:2534–2538 (Oct. 1987).
(5) Macrina, Francis L., et al., Gene, 19:345–353 (1982).
(6) Macrina, Francis L., et al., Gene, 25:145–150 (1983).
(7) Tobian, Janet Ash, et al., Journal of Bacteriology, 160:556–563 (Nov. 1984).
(8) Bachman, K., Ptashne M., and Gilbert, W. Proc. Natl. Acad. Sci USA 73:4174–4178 (1976).

*Pediococcus* spp. were routinely maintained on MRS agar (Difco Laboratories, Detroit, Mich.). *Escherichia coli* strains were routinely carried on Lennox L agar (Gibco/BRL, Gaithersburg, Md.). *Escherichia coli* strains were also grown on modified MRS agar (no citrate or acetate) or in M9 medium (Maniatis, T., E. F. Fritsch, and J. Sambrook, Molecular cloning: a laboratory manual. Cold Spring Harbor Laboratory, Cold Spring Harbor, N.Y. (1982)) supplemented with 1% yeast extract (Oxoid, Ltd., Basingstoke, Hampshire, U.K.) and 1% Hy Case ™ (Sheffield Products, Norwich, N.Y.) for bacteriocin assays. Selective antibiotic concentrations were as follows: ampicillin, 25 ug/ml; tetracycline, 10 ug/ml; erythromycin, 50 ug/ml; and chloramphenicol, 25 ug/ml. All antibiotics were purchased from Sigma Chemical Co., St. Louis, Mo.

Bacteriocin assays. Production of bacteriocin was assayed as previously described (Gonzalez, C. F., and B. S. Kunka, Appl. Environ. Microbiol. 53:2534–2538 (1987)). Strains were patched on MRS agar or modified MRS agar for *Escherichia coli* and incubated at 35° C. for 18 hours. The plates were then overlaid with soft agar (0.8%) seeded with indicator cells. Isolates which produced a clear, defined zone of inhibition were considered as bacteriocin producers.

One arbitrary unit (AU) of bacteriocin was defined as 5 microliters of the highest dilution of culture supernatant yielding a definite zone of growth inhibition on the indicator lawn. The titer was expressed as the reciprocal of the highest dilution showing inhibition.

Isolation and analysis of plasmid DNA. Covalently closed circular plasmid DNA was isolated from *Escherichia coli* by the method of Clewell and Helinski (Clewell, D. B., and D. R. Helinski, Biochemistry 9:4428–4440 (1970)). *Escherichia coli* strains were screened for plasmid content as previously described (Macrina, F. L., J. A. Tobian, K. R. Jones, R. P. Evans, and D. B. Clewell, Gene 19:345–353 (1982)). Pediococus plasmid DNA was obtained by a scaled up modification of the LeBlanc and Lee procedure (LeBlanc, D. J., and L. N. Lee, J. Bacteriol. 140:1112-1115 (1979)) as described by Gonzalez and Kunka (Gonzalez, C. F., and B. S. Kunka, Appl. Environ. Microbiol. 46:81-89 (1983)). Plasmid DNA and restriction endonuclease digests were analyzed by agarose gel electrophoresis on 0.8% agarose (Bethesda Research Laboratories, Inc., Gaithersburg, Md.) slab gels. Size standards were *Escherichia coli* V517 (Macrina, F. L., D. J. Kopecko, K. R. Jones, D. J. Ayers, and S. McCowen, Plasmid 1:417-420 (1978)) for undigested plasmid DNA and HindIII -digested bacteriophage lambda DNA (Bethesda Research Laboratories) for restriction endonuclease-cleaved plasmid DNA.

DNA enzymology. Restriction endonuclease digestions were performed in low-, medium-, or high-salt buffers, as recommended by Maniatis et al. (Maniatis, T., E. F. Fritsch, and J. Sambrook, Molecular cloning: a laboratory manual. Cold Spring Harbor Laboratory, Cold Spring Harbor, N.Y. (1982)) . Restriction enzymes were obtained from Bethesda Research Laboratories. DNA ligation reactions were carried out with T4 DNA ligase (Bethesda Research Laboratories) at 4° C. for 18 hours according to conditions recommended by the manufacturer.

Bacterial transformations. *Escherichia coli* was transformed by the $CaCl_2$ heat shock method (Molecular cloning: a laboratory manual. Cold Spring Harbor Laboratory, Cold Spring Harbor, N.Y. (1982)) with cells harvested at an optical density at 660 nm of 0.2 to 0.3.

Purification of PA-1. Cultural Supernatant was neutralized to pH 6.0 with sodium hydroxide prior to gel filtration. A 450 ml aliquot of neutralized supernatant was applied to a 5 cm×55 cm column (Pharmacia) containing one liter of Spectra/Gel AcA 202 (Spectrum) gel filtration resin which had been equilibrated with 0.05M 2-(N-morpholino)ethanesulfonic acid (MES), pH 6.0. Activity was eluted using the same buffer. Active fractions were pooled and applied to a 2.5 cm×90 cm CM-Sepharose column equilibrated with 0.05M MES, pH 6.0. Activity was eluted with a linear gradient to 0.05M MES containing 1M sodium chloride, pH 6.0. Active fractions were pooled and dialyzed against a 10 fold excess of water using 1000 Da molecular weight cut-off dialysis tubing (Spectra-Por 6, Spectrum). Dialysate volume was reduced 12 fold by applying the dialysis tubing directly to solid 20 KDa polyethylene glycol (Carbowax, Union Carbide) and was then further reduced 3.5 fold by vacuum centrifugation (Speed-Vac, Savant). Concentrated PA-1 was applied to a 1.0 cm×25 cm C18 reversed-phase column (Vydac) equilibrated with 0.1% aqueous trifluoroacetic acid. Activity was eluted with a linear gradient to 45% acetonitrile over 30 minutes at 1.5 ml/min. Active fractions were determined by directly spotting aliquots of column effluent on MRS plates overlaid with soft agar containing indicator cells. Active fractions were dried by vacuum centrifugation and stored at −20° C. Specific activity is defined as AU per milligram protein. Protein analyses were performed using the BCA protein assay kit (Pierce) using directions supplied with the kit.

EXAMPLE 1

Restriction endonuclease map of pSRQ11. The genes involved in bacteriocin PA-1 activity were previously shown to be associated with the presence of a 9.0 kilobase plasmid, designated pSRQ11 (Gonzalez, C. F., and B. S. Kunka, Appl. Environ. Microbiol. 53:2534-2538 (1987)). Plasmid pSRQ11 was digested with a number of restriction endonucleases to generate the restriction site map shown in FIG. 1. The plasmid contained several unique sites including EcoRI, NdeI, XbaI, SalI, and SstI. Other restriction enzymes which cleaved the plasmid were ClaI, HindIII, PvuII, and EcoRV. The following restriction sites were not found on pSRQ11: AvaI, BamHI, SphI, NruI, PstI, and BglII.

EXAMPLE 2

Expression of PA-1 bacteriocin in *E. coli*. Plasmid pSRQ11 was digested with EcoRI and cloned into the EcoRI site on plasmid pVA891 (Macrina, F. L., et al., Gene 25:145-150 (1983)), which contains an erythromycin resistance marker expressed in both *Escherichia coli* and streptococci. Recombinant plasmids were obtained with pSRQ11 inserted in both orientations and were designated pSRQ11.1 and pSRQ11.2 as shown in FIG. 2. These *Escherichia coli* strains were assayed for expression of the PA-1 bacteriocin as previously described (Gonzalez, C. F., and B. S. Kunka, Appl. Environ. Microbiol. 53:2534-2538 (1987)). The strains were grown on modified MRS medium and overlaid with *Pediococcus pentosaceus* FBB63 indicator strain. *Escherichia coli* trains containing pSRQ11.1 and pSRQ11.2 both produced zones of inhibition in the indicator lawn while the control *Escherichia coli* V850 strains showed no zone of inhibition (Table 2).

TABLE 2

| Plasmids derived from pSRQ 11 | | | |
|---|---|---|---|
| Name | Fragment | Vector | Bacteriocin Activity |
| pSRQ11.1 | EcoRI nicked pSRQ11 | pVA891 | + |
| pSRQ11.2 | EcoRI nicked pSRQ11 (opposite orientation from pSRQ11.1) | pVA891 | + |
| pSRQ11.11 | Sal I deletion of pSRQ11.1 | pVA891 | + |
| pSRQ11.12 | PvuII deletion of pSRQ11.1 | pVA891 | − |
| pSRQ11.13 | PvuII deletion of pSRQ11.1 | pVA891 | − |
| pSRQ11.21 | Sal I deletion of pSRQ11.2 | pVA891 | − |
| pSRQ11.22 | PvuII deletion of pSRQ11.2 | pVA891 | − |
| pSRQ161 | EcoRI nicked pSRQ11 | pSA3 | + |
| pSRQ210 | 3.7 kbp XbaI—Sal I | pACYC184 | − |
| pSRQ211 | 2.7 kbp HindIII fragment C | pACYC184 | − |
| pSRQ220 | 5.6 kbp EcoRI—Sal I | pBR322 | + |
| pSRQ220.1 | Cla I deletion of pSRQ220 | pBR322 | − |
| pSRQ220.2 | HindIII deletion of pSRQ220 | pBR322 | − |
| pSRQ220.3 | PvuII deletion of pSRQ220 | pBR322 | − |
| pSRQ221 | pACYC184 in XbaI site of pSRQ220 | pBR322 | − |
| pSRQ221.1 | XbaI deletion of pSRQ221 | pBR322 | + |
| pSRQ222 | pACY184 XbaI—EcoRI fragment in pSRQ220 | pBR322 | − |
| pUR5204 | 1.3 kbp HindIII—Sal I deletion derivative of pSRQ220 | pBR322 | − |
| pUR5205 | pSRQ220 derivative with disrupted HindIII site in ORF 3 | pBR322 | − |
| pUR5206 | pSRQ220 derivative with disrupted HindIII site in ORF 2 | pBR322 | + |
| pUR5217 | pSRQ220 derivative with BamHI linker insertion in Bal I site of ORF 1 | pBR322 | − |

The plasmid pSRQ11 was also cloned in the unique EcoRI site of the *E. coli*-Streptococcus shuttle plasmid pSA3. The resulting clone was called pSRQ161. When the *E. coli* V850 strain carrying pSRQ161 (Table 2) was grown overnight in M9 medium supplemented with 1% yeast extract and 1% Hy Case, the filter sterilized culture supernatant yielded approximately 400 AU/ml of the bacteriocin PA-1. This observation indicated that *E. coli* V850 (pSRQ161) was producing and excreting PA-1 into the media. Also, other *E. coli* strains were transformed with the plasmid pSRQ161 and observed to produce PA-1. From this data, it was concluded that a gene fragment encoding bacteriocin PA-1 from *P. acidilactici* PAC 1.0 can be expressed and is functional in an *E. coli* host strain.

EXAMPLE 3

Deletion derivative analysis of pSRQ11 subclones.

In order to localize the region encoding the PA-1 gene(s), SalI and PvuII deletion derivatives of pSRQ11.1 and pSRQ11.2 were obtained (FIG. 2). The SalI deletion of pSRQ11.1 retained activity while the PvuII deletion derivatives displayed no zones of inhibition against the indicator strain (Table 2). Both the PvuII and SalI deletion derivatives of pSRQ11.2 expressed no PA-1 activity (Table 2). These data suggested that the bacteriocin gene was located on the approximately 5.6 kbp EcoRI-SalI fragment of pSRQ11.1 as shown in FIG. 2. This 5.6 kbp EcoRI-SalI fragment then was subcloned into the EcoRI and SalI restriction sites on the *Escherichia coli* plasmid pBR322 (Bolivar et al., Gene 2:95-113 (1977)), and the resulting chimeric plasmid was designated pSRQ220 (FIG. 3A). The *Escherichia coli* strain containing pSRQ220 was assayed and found to express bacteriocin activity. Two additional deletion derivatives of pSRQ220, i.e., a plasmid derivative lacking a 2.7 kbp HindIII fragment and a plasmid derivative lacking a 1.3 kbp HindIII-SalI fragment (FIG. 3B), were assayed and both found to be negative for PA-1 activity. Also the following deletion derivatives were obtained: pSRQ210, which consisted of the pSRQ11, XbaI-SalI fragment cloned into *E. coli* vector pACYC184 (Chang, A. C. Y., et al. J. Bacteriol. 134:1141-1156 (1978)), and pSRQ211, which consisted of pSRQ11 HindIII fragment c (from map coordinates 1.5 to 4.2, FIG. 1) also cloned into pACYC184. Neither of these two strains expressed PA-1 activity. Together with the bacteriocin PA-1 negative PvuII and ClaI deletion derivatives (FIGS. 2A, and 3B (Table 2)), these results show that several genes, or one very long gene (or operon), present on the 5.6 kbp EcoRI-SalI fragment, are responsible for PA-1 activity.

EXAMPLE 4

Insertional inactivation of bacteriocin PA-1 production. Since the XbaI restriction site is unique on both pSRQ11 and pSRQ220 and lies within the region involved in PA-1 production, it was chosen as a site to insert a foreign DNA fragment and interrupt transcription of the bacteriocin gene. Plasmid pACYC184, approximately 4 kbp in size and also containing a single XbaI site, was cloned into the XbaI site on pSRQ220. The strain containing the resulting recombinant plasmid, pSRQ221, was assayed for PA-1 activity and proved negative (Table 2). When the pACYC184 insert was removed by XbaI digestion, followed by religation, resulting in pSRQ 221.1, activity was once again restored. Another construct where the XbaI-EcoRI fragment of pSRQ220 was replaced by the XbaI-EcoRI fragment of pACYC184 also was negative for bacteriocin activity (Table 2).

EXAMPLE 5

The DNA sequence of the 5.6 kbp SalI-EcoRI DNA fragment, as present on plasmid pSRQ220, was established by the Sanger dideoxy chain termination procedure (Sanger, F., Nicklen, S., and Coulson, A. R., Proc. Natl. Acad. Sci. USA, 74:5463-3967 (1977)) with the modifications as described by Biggin et al (Biggin, M. D. et al., Proc. Natl. Acad. Sci. USA, 80:3963-3965 (1983)), using alpha-35S-dATP (2000 Ci/mmol) and Klenow enzyme (Amersham), ddNTP's (Pharmacia-PL Biochemicals) and dNTP's (Boehringer). The sequencing reaction products were separated on a denaturing polyacrylamide gel with a buffer gradient as described by Biggin et al. (Biggin, M. D. et al., Proc. Natl. Acad. Sci. USA, 80:3963-3965 (1983)). Purified, double-stranded plasmid DNA of pSRQ220 served as template in the sequence reaction, following the procedure described by Hattori and Sakaki (Hattori, M., and Sakaki, Y., Anal. Biochem. 152:232-238 (1986)). Deoxy-oligonucleotide primers were synthesized on a DNA-synthesizer (Applied Biosystems 380A) using the Phosphoamidit technique (Barone, A. D. et al., Nucleic Acid Research, 12:4051-4061 (1984)).

The DNA sequence when translated in all possible reading frames revealed at least three open reading frames. (FIGS. 4A to Q). The first open reading frame (ORF 1) encodes a protein which consists of 62 amino acid residues followed by a TAG stop codon (FIGS. 4A to Q). The second open reading frame (ORF 2), positioned just downstream of ORF 1, codes for a protein which consists of 112 amino acid residues followed by a TAG stop codon (FIGS. 4A to Q). Further downstream the third open reading frame (ORF 3) predicts a protein consisting of 724 amino acid residues with a TAG stop codon (FIGS. 4A to Q).

ORF 1 encodes a protein of 62 amino acids of which amino acid residues 19 to 62 correspond entirely with the amino acid sequence of a protein, which was isolated from *P. acidilactici* NRRL-B-18050 called bacteriocin PA-1, and which, when separated on a polyacrylamide gel, inhibited *P. pentosaceus* FBB-63 effectively in an overlay experiment which is the subject of U.S. application Ser. No. 514,102 (FIG. 4, and FIG. 5). This proves that ORF 1 encodes a precursor of bacteriocin PA-1, containing an 18 amino acid N-terminal peptide which is cleaved off during the process of synthesis or excretion.

Both the PvuII deletion derivative pSRQ11.13 and the HindIII deletion derivative pSRQ220.2 (Table 2; FIG. 3B) result in a loss of PA-1 bacteriocin activity. As these deletions disturb both ORF 2 and ORF 3, or ORF 3 only, but not the PA-1 bacteriocin encoding gene (ORF 1), it can be concluded that also the presence of either ORF 2 or ORF 3, or both is necessary for PA-1 bacteriocin activity.

EXAMPLE 6

Site-specific mutagenesis of genes involved in PA-1 bacteriocin production.

The specific role in PA-1 bacteriocin production of each of the open reading frames was determined by introduction of frameshift mutations in the various genes.

Plasmid pSRQ220 contains two sites for the restriction enzyme BalI. One is situated in the pBR332-part of the plasmid, whereas the other is positioned within ORF 1 which encodes the PA-1 bacteriocin (FIG. 3A, and 3B). A frameshift mutation in ORF 1 was introduced by insertion of a double-stranded oligonucleotide linker fragment with the sequence 5'-TGCATG-GATCCTGATC-3' into this BalI-site. Plasmid pSRQ220 was therefore partially digested with BalI, generating linear blunt-ended DNA molecules. This was achieved by incubation of the plasmid DNA in a restriction buffer for a short time period using only low amounts of the restriction enzyme. The linker fragment was added and allowed to ligate with the BalI-treated vector DNA. Insertion of the linker fragment disrupts the BalI site, but introduces a new and unique BamHI site into the plasmid, that was used for identification of the desired mutant. After transformation of the ligation mixture, plasmid DNA was isolated from the transformants and screened for the presence of a BamHI site, concomitant with the loss of a BalI site. In this way plasmid pUR5217 was identified which carried the desired linker insertion within ORF 1. Introduction of the mutation was confirmed by determination of the nucleotide sequence around the restriction site of the mutant. E. coli cells containing pUR5217 were assayed for PA-1 bacteriocin activity and found to have lost this property. This result is in good agreement with the previous obtained deletion data and it again proves that the presence of ORF 1 is essential for PA-1 activity. Restriction enzyme HindIII has only two restriction sites in pSRQ220, one of which is positioned in ORF 2, while the other is positioned in ORF 3 (FIG. 3B). These sites were therefore well suited for introduction of mutations in these genes. Plasmid pSRQ220 was partially digested with HindIII, as described above. To fill in the 3'-restriction ends Klenow enzyme and a mixture of the four dNTP's (A, T, G, C, 1 mM each) were added to the DNA-sample, followed by incubation at 37° C. for 30 minutes. After ligation for 16 hours at 15° C. the DNA-mixture was transformed to E. coli 294. Plasmid DNA was isolated from the transformants and screened for the loss of the HindIII restriction sites by digesting with HindIII. Introduction of the mutations was confirmed by determination of the nucleotide sequence around the restriction site of each mutant. In this way plasmid pUR5206 which carried a mutation at the HindIII site in ORF 2, and plasmid pUR5205 which carried a mutation at the HindIII site in ORF 3 were identified. E. coli cells containing pUR5206 were assayed and found to express PA-1 bacteriocin activity, whereas E. coli cells containing pUR5205 were negative for PA-1 bacteriocin activity. From these data it can be concluded that, besides the presence of the PA-1 bacteriocin gene (ORF 1), also the presence of an intact ORF 3 is needed for PA-1 bacteriocin activity. The function of ORF 2 is not known. Although E. coli cells containing pUR5206 are able to produce bacteriocin PA-1 activity, it cannot be ruled out that ORF 2 is involved in the secretion or processing of bacteriocin PA-1. From the nucleotide sequence analysis some other tentative open reading frames can be deduced (data not shown). Therefore it is possible that other information is present on the 5.6 kbp EcoRI-SalI fragment which is also needed for PA-1 bacteriocin activity.

It is intended that the foregoing description be only illustrative of the present invention and the present invention is limited only by the hereinafter appended claims.

We claim:

1. A nucleic acid corresponding to the nucleic acid free of nucleic acids encoding other proteins which can be isolated from a strain belonging to the genus Pediococcus, the nucleic acid containing only genes coding for both a bacteriocin precursor having the amino acid sequence encoded by ORF1 of SEQ ID NO: 1 or a bacteriocin precursor differing from said bacteriocin precursor by one or more conservative amino acid substitutions, and a gene for at least one other protein selected from the group consisting of ORF2, ORF3, and ORF2 and ORF3 as given in SEQ ID NO: 1.

2. The nucleic acid according to claim 1, in which the Pediococcus is *Pediococcus acidilactici*.

3. The nucleic acid according to claim 1, in which the Pediococcus is *Pediococcus acidilactici* NRRL-B-18050.

4. The nucleic acid according to claim 1 containing the three open reading frames, ORF1, ORF2 and ORF3 as given in SEQ ID NO: 1, and derived from the plasmid pSRQ11.

5. The nucleic acid according to claim 1 containing the 5.6 kbp EcoRI-SalI DNA fragment of plasmid pSRQ11 as given in SEQ ID NO: 1.

6. The nucleic acid according to claim 1 also containing transcriptional and translational initiation and termination sequences of open reading frames as given in SEQ ID NO: 1.

7. An isolated nucleic acid encoding only a bacteriocin precursor, said nucleic acid being selected from the group consisting of ORF1 in SEQ ID NO: 1, and modifications thereof that encode a protein still having the capability of being converted into an active bacteriocin.

8. A vector, that can be stably maintained in a host microorganism, which vector can be maintained as a plasmid or can integrate into a chromosome of the host microorganism, comprising the nucleic acid according to claim 1 in the vector.

9. The vector according to claim 8, in which the nucleic acid contains open reading frames ORF1 and ORF3, and optionally ORF 2 as given in SEQ ID NO: 1.

10. A vector according to claim 9 containing the 5.6 kbp EcoRI-SalI fragment as given in SEQ ID NO: 1.

11. The vector according to claim 8 containing ORF1, and optionally ORF2 or ORF3 or both, as given in SEQ ID NO: 1, in which the ORFs are under control of one or more promoter systems functional in said host microorganism and at least after the most down stream ORF of ORF1, ORF2 or ORF3 a terminator sequence is present, wherein the ORF1 can have a promoter system, optionally followed by a terminator sequence, or ORF1 can form part of an operon containing ORF2 or ORF3, or ORF2 and ORF3 together.

12. A microorganism transformed by introducing the vector of claim 8, capable of producing a bacteriocin.

13. A microorganism transformed by introducing the vector of claim 9, capable of producing a bacteriocin.

14. A microorganism transformed by introducing the vector of claim 10, capable of producing a bacteriocin.

15. A microorganism transformed by introducing the vector of claim 11, capable of producing a bacteriocin.

16. A microorganism according to claim 12 selected from the group consisting of the genera Lactococcus, Lactobacillus, Leuconostoc, Streptococcus, Pediococcus, Escherichia and yeasts.

17. The vector of claim 8 that replicates or is stably maintained in the microorganism selected from the group consisting of the genera Lactococcus, Lactobacillus, Leuconostoc, Streptococcus, Pediococcus, Escherichia and yeasts.

18. The vector of claim 8 which replicates or is stably maintained in the microorganism which expresses the bacteriocin.

19. An isolated nucleic acid encoding a protein essential for obtaining a functional active bacteriocin, said protein having the amino acid sequence encoded by ORF3 of SEQ ID NO: 1 or a protein differing from said protein by one or more consecutive amino acid substitutions and still having the capability of assisting in production of an active bacteriocin.

20. An isolated nucleic acid encoding a protein having the amino acid sequence encoded by ORF2 as given in SEQ ID NO: 1.

21. The nucleic acid of claim 1 derived by a polymerase chain reaction method.

22. An isolated nucleic acid as given in SEQ ID NO; 1.

23. A nucleic acid free of nucleic acids encoding other proteins, said nucleic acid encoding a protein having an amino acid sequence selected from the group of ORF1, ORF2, and ORF3 as given in SEQ ID NO: 1.

* * * * *

UNITED STATES PATENT AND TRADEMARK OFFICE
CERTIFICATE OF CORRECTION

PATENT NO. : 5,260,212
DATED : November 9, 1993
INVENTOR(S) : John D. Marugg, Adrianus M. Ledeboer, Peter A. Vandenbergh and James T. Henderson It is certified that error appears in the above—identified patent and that said Letters Patent is hereby corrected as shown below:

Column 2, line 30, "richia", should be --Escherichia--.

Column 2, line 60, after "represent", --three-- should be inserted.

Column 3, line 1, "staned" should be --stained--.

Column 3, line 18 "decribed", should be --described--.

Column 4, line 6 (Table 1), " 9.0 kbo" should be --9.0 kbp--.

Column 4, line 13, "V851" should be --V871--.

Column 6, line 10, "BgllII", should be --BglII--.

UNITED STATES PATENT AND TRADEMARK OFFICE
CERTIFICATE OF CORRECTION

PATENT NO. : 5,260,212

DATED : November 9, 1993

INVENTOR(S) : John D. Marugg, Adrianus M. Ledeboer, Peter A. Vandenbergh and James T. Henderson It is certified that error appears in the above—identified patent and that said Letters Patent is hereby corrected as shown below:

Column 6, line 27, "trains" should be --strains--.

Column 6, line 53, "pACY184" should be --pACYC184--.

Column 8, line 2, the following heading should be inserted -- Nucleotide sequence analysis of pSRQ220--.

Column 19, line 52 (Claim 10), "Claim 9" should be --Claim 8--.

Column 20, line 42 (Claim 19), "consecutive", should be --conservative--.

Signed and Sealed this

Twenty-eighth Day of June, 1994

Attest:

BRUCE LEHMAN

Attesting Officer

Commissioner of Patents and Trademarks